United States Patent
Raymon

(10) Patent No.: US 9,782,427 B2
(45) Date of Patent: Oct. 10, 2017

(54) METHODS FOR TREATING CANCER USING TOR KINASE INHIBITOR COMBINATION THERAPY

(71) Applicant: Signal Pharmaceuticals, LLC, San Diego, CA (US)

(72) Inventor: Heather Raymon, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 346 days.

(21) Appl. No.: 14/254,009

(22) Filed: Apr. 16, 2014

(65) Prior Publication Data

US 2014/0315848 A1 Oct. 23, 2014

Related U.S. Application Data

(60) Provisional application No. 61/813,053, filed on Apr. 17, 2013.

(51) Int. Cl.

| A61K 31/4985 | (2006.01) |
|---|---|
| A01N 43/04 | (2006.01) |
| A61K 31/706 | (2006.01) |
| A61K 31/5025 | (2006.01) |
| A61K 45/06 | (2006.01) |
| A61K 31/472 | (2006.01) |
| A61K 31/7068 | (2006.01) |
| A61K 33/42 | (2006.01) |

(52) U.S. Cl.
CPC .......... *A61K 31/706* (2013.01); *A61K 31/472* (2013.01); *A61K 31/4985* (2013.01); *A61K 31/5025* (2013.01); *A61K 31/7068* (2013.01); *A61K 33/42* (2013.01); *A61K 45/06* (2013.01)

(58) Field of Classification Search
CPC .............. A61K 31/706; A61K 31/5025; A61K 31/472; A61K 31/4985; A61K 31/7068; A61K 33/42; A61K 45/06; A61K 2300/00
See application file for complete search history.

(56) References Cited

U.S. PATENT DOCUMENTS

| 3,507,866 A | 4/1970 | Jones et al. |
|---|---|---|
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,791,006 B2 | 9/2004 | Nezu et al. |
| 6,800,436 B1 | 10/2004 | Jenne et al. |
| 6,855,723 B2 | 2/2005 | McMahon et al. |
| 7,608,622 B2 | 10/2009 | Liu et al. |
| 8,110,578 B2 * | 2/2012 | Perrin-Ninkovic .. C07D 487/04 514/252.11 |
| 8,158,605 B2 * | 4/2012 | Silverman .............. A61K 31/53 514/43 |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,569,494 B2 * | 10/2013 | Harris .................. C07D 487/04 544/350 |
| 9,493,466 B2 * | 11/2016 | Xu ....................... C07D 487/04 |
| 2003/0036652 A1 | 2/2003 | Bakthavatchalam et al. |
| 2003/0162968 A1 | 8/2003 | Cirillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2005/0009737 A1 | 1/2005 | Clark |
| 2006/0004014 A1 | 1/2006 | Hoffmann et al. |
| 2006/0135511 A1 | 6/2006 | Burgey |
| 2006/0142269 A1 | 6/2006 | Dykes |
| 2006/0211702 A1 | 9/2006 | Oslob et al. |

(Continued)

FOREIGN PATENT DOCUMENTS

| CA | 2 458 699 | 3/2003 |
|---|---|---|
| DE | 262 026 | 11/1988 |

(Continued)

OTHER PUBLICATIONS

U.S. Appl. No. 15/277,285, dated Sep. 2016, Xu et al.*
Boulay et al., "Dual Inhibition of mTOR and Estrogen Receptor Signaling in vitro Induces Cell Death inModels of Breast Cancer" Clinical Cancer Research (2005) vol. 11 No. 14 pp. 5319-5328.*
Levenson et al., "MCF-7: The First Hormone-Responsive Breast Cancer Cell Line" Cancer Research (1997) vol. 57 pp. 3071-3078.*
U.S. Appl. No. 14/055,995, filed Oct. 17, 2013, Signal Pharmaceutical, LLC.

(Continued)

*Primary Examiner* — Eric Olson
(74) *Attorney, Agent, or Firm* — Jones Day

(57) ABSTRACT

Provided herein are methods for treating or preventing a cancer, comprising administering an effective amount of a TOR kinase inhibitor having the following formula (I):

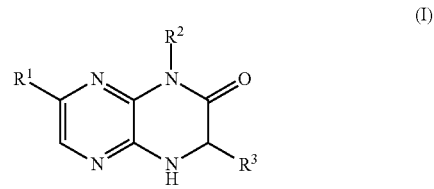

Figure 1:
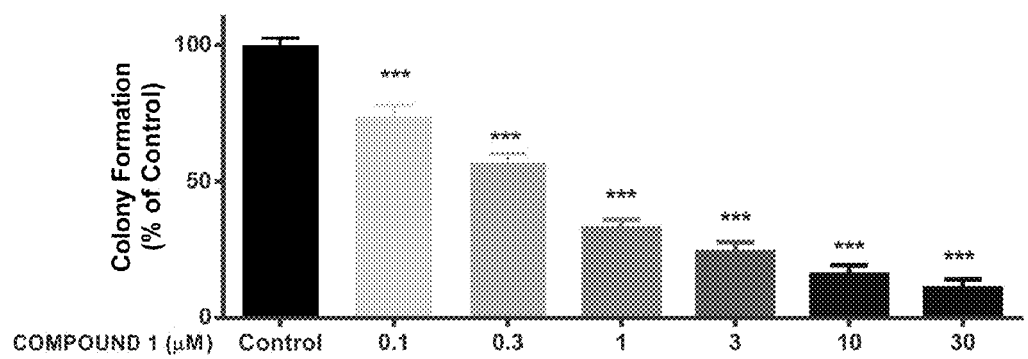

and an effective amount of a cytidine analog, such as 5-azacytidine, to a patient having a cancer.

9 Claims, 6 Drawing Sheets

(56) References Cited

U.S. PATENT DOCUMENTS

| | | |
|---|---|---|
| 2007/0036793 A1 | 2/2007 | Hardie et al. |
| 2007/0112005 A1 | 5/2007 | Chen et al. |
| 2008/0194019 A1 | 8/2008 | Cantley et al. |
| 2008/0214580 A1 | 9/2008 | Neagu et al. |
| 2009/0023724 A1 | 1/2009 | Mortensen et al. |
| 2009/0042890 A1 | 2/2009 | Mortensen et al. |
| 2009/0069289 A1 | 3/2009 | Neagu et al. |
| 2009/0163545 A1 | 6/2009 | Goldfard |
| 2009/0181963 A1 | 7/2009 | Dehnhardt et al. |
| 2009/0209482 A1 | 8/2009 | Silverman et al. |
| 2009/0281075 A1 | 11/2009 | Roughton et al. |
| 2010/0144738 A1 | 6/2010 | Bornmann et al. |
| 2010/0216781 A1 | 8/2010 | Perrin-Ninkovic et al. |
| 2010/0249122 A1 | 9/2010 | Kalman |
| 2011/0137028 A1 | 6/2011 | Harris et al. |
| 2011/0257167 A1 | 10/2011 | Chopra et al. |
| 2011/0318336 A1 | 12/2011 | Petricoin, III et al. |
| 2012/0028972 A1 | 2/2012 | Wong et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1* | 8/2013 | Xu .................. A61K 31/4985 514/43 |
| 2013/0245026 A1 | 9/2013 | Xu et al. |
| 2013/0245027 A1* | 9/2013 | Xu .................. A61K 31/4985 514/249 |
| 2013/0245028 A1 | 9/2013 | Xu et al. |
| 2013/0245029 A1 | 9/2013 | Xu et al. |

FOREIGN PATENT DOCUMENTS

| | | | |
|---|---|---|---|
| EP | 0 385 850 | 9/1990 | |
| JP | 63275582 | 5/1987 | |
| JP | 2001048882 | 2/2001 | |
| JP | 2002100363 | 4/2002 | |
| JP | 2002167387 | 6/2002 | |
| WO | WO 99/16438 | 4/1999 | |
| WO | WO 99/28320 | 6/1999 | |
| WO | WO 99/28459 | 6/1999 | |
| WO | WO 00/73306 | 12/2000 | |
| WO | WO 02/48152 | 6/2002 | |
| WO | WO 02/076954 | 10/2002 | |
| WO | WO 03/032989 | 4/2003 | |
| WO | WO 03/072557 | 9/2003 | |
| WO | WO 03/093290 | 11/2003 | |
| WO | WO 2004/042002 | 5/2004 | |
| WO | WO 2004/048365 | 6/2004 | |
| WO | WO 2004/065378 | 8/2004 | |
| WO | WO 2004/076454 | 9/2004 | |
| WO | WO 2004/078754 | 9/2004 | |
| WO | WO 2004/085409 | 10/2004 | |
| WO | WO 2004/096797 | 11/2004 | |
| WO | WO 2005/003147 | 1/2005 | |
| WO | WO 2005/021519 | 3/2005 | |
| WO | WO 2005/120511 | 12/2005 | |
| WO | WO 2006/001266 | 1/2006 | |
| WO | WO 2006/018182 | 2/2006 | |
| WO | WO 2006/030031 | 3/2006 | |
| WO | WO 2006/036883 | 4/2006 | |
| WO | WO 2006/045828 | 5/2006 | |
| WO | WO 2006/046031 | 5/2006 | |
| WO | WO 2006/050076 | 5/2006 | |
| WO | WO 2006/065703 | 6/2006 | |
| WO | WO 2006/087530 | 8/2006 | |
| WO | WO 2006/090167 | 8/2006 | |
| WO | WO 2006/090169 | 8/2006 | |
| WO | WO 2006/091737 | 8/2006 | |
| WO | WO 2006/108103 | 10/2006 | |
| WO | WO 2007/044698 | 4/2007 | |
| WO | WO 2007/044729 | 4/2007 | |
| WO | WO 2007/044813 | 4/2007 | |
| WO | WO 2007/047754 | 4/2007 | |
| WO | WO 2007/060404 | 5/2007 | |
| WO | WO 2007/066099 | 6/2007 | |
| WO | WO 2007/066102 | 6/2007 | |
| WO | WO 2007/080382 | 7/2007 | |
| WO | WO 2007/125321 | 11/2007 | |
| WO | WO 2007/129044 | 11/2007 | |
| WO | WO 2007/129052 | 11/2007 | |
| WO | WO 2007/129161 | 11/2007 | |
| WO | WO 2007/135398 | 11/2007 | |
| WO | WO 2008/016669 | 2/2008 | |
| WO | WO 2008/023161 | 2/2008 | |
| WO | WO 2008/032027 | 3/2008 | |
| WO | WO 2008/032028 | 3/2008 | |
| WO | WO 2008/032033 | 3/2008 | |
| WO | WO 2008/032036 | 3/2008 | |
| WO | WO 2008/032060 | 3/2008 | |
| WO | WO 2008/032064 | 3/2008 | |
| WO | WO 2008/032072 | 3/2008 | |
| WO | WO 2008/032077 | 3/2008 | |
| WO | WO 2008/032089 | 3/2008 | |
| WO | WO 2008/032091 | 3/2008 | |
| WO | WO2008/051493 | * 5/2008 | ........... C07D 498/04 |
| WO | WO 2008/051493 | 5/2008 | |
| WO | WO 2008/064093 | 5/2008 | |
| WO | WO 2008/115974 | 9/2008 | |
| WO | WO 2008/140947 | 11/2008 | |
| WO | WO 2009/007748 | 1/2009 | |
| WO | WO 2009/007750 | 1/2009 | |
| WO | WO 2009/007751 | 1/2009 | |
| WO | WO 2009/052145 | 4/2009 | |
| WO | WO 2009/102986 | 8/2009 | |
| WO | WO 2010/006072 | 1/2010 | |
| WO | WO2010/062571 | * 6/2010 | ........... C07D 487/04 |
| WO | WO 2010/062571 | 6/2010 | |
| WO | WO 2010/068483 | 6/2010 | |
| WO | WO 2011/031965 | 3/2011 | |
| WO | WO 2011/079114 | 6/2011 | |
| WO | WO 2011/097333 | 8/2011 | |
| WO | WO2013/059396 | * 4/2013 | ......... A61K 31/4166 |

OTHER PUBLICATIONS

U.S. Appl. No. 14/254,001, filed Apr. 16, 2014, Signal Pharmaceutical, LLC.
U.S. Appl. No. 14/254,004, filed Apr. 16, 2014, Signal Pharmaceutical, LLC.
U.S. Appl. No. 14/254,015, filed Apr. 16, 2014, Signal Pharmaceutical, LLC.
U.S. Appl. No. 14/254,017, filed Apr. 16, 2014, Signal Pharmaceutical, LLC.
U.S. Appl. No. 14/254,019, filed Apr. 16, 2014, Signal Pharmaceutical, LLC.
U.S. Appl. No. 14/254,010, filed Apr. 16, 2014, Signal Pharmaceutical, LLC.
U.S. Appl. No. 14/254,020, filed Apr. 16, 2014, Signal Pharmaceutical, LLC.
U.S. Appl. No. 14/254,023, filed Apr. 16, 2014, Signal Pharmaceutical, LLC.
Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.

(56) References Cited

OTHER PUBLICATIONS

Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_N$ -$S_N$ ipsoand $S_N^H$ -$S_N$ ipsoreactions," J. of Heterocyclic Chemistry, vol. 38(4):901-907.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews/Drug Discovery, vol. 1:309-315.
Cohen, 2005, *Protein Kinase Inhibitors for the Treatment of Disease: The Promise and the Problems*, Handbook of Experimental Pharmacology, Springer Berlin Heidelberg, 167:1-7.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels-alder reaction," J. Am Chem Soc., vol. 121(24):5833-5834.
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1978:433195 (XP-002472262) (1978).
Database CAPLUS Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Georgakis and Younes, 2006, "From rapi nui to rapamycin: targeting PI3K/Akt/mTOR for cancer therapy," Expert Rev. Anticancer Ther., vol. 6(1):131-140.
Grimmiger et al., 2010, " Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-($N^1$ -tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62, (2004).
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.

Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Yuan et al., 2009, "Targeting tumorigenesis: development and use of mTOR inhibitors in cancer therapy," Journal of Hematology & Oncology, Biomed Central Ltd., London UK, vol. 2(1): 45.
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1): 91-99.
Shaw et al., 2009, "LKB1 and AMP-activated protein kinase control of mTOR signalling and growth," Acta. Physiol (Oxf.) 196(1):65-80.
Singh et al., 1994, "Novel cAMP PDE III Inhibitors: Imidazo[4,5-b]pyridin-2(3H)-ones and Thiazolo[4,5- b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.

(56) References Cited

OTHER PUBLICATIONS

Yoneda et al., 1976, "A transformationof 7-azapteridines into 6-azapurines (Imidazo[4,5-e]-as-triazines)," Heterocycles, vol. 4(9):1503-1508.

Yoneda et al., 1978, "Synthesis of imadazo[4,5-e]-as-triazine (6-Azapurine) Deriviatives," Chem & Pharm Bulletin, vol. 26(10):3154-3160.

Zaki et al., 2007, "The synthesis of imidazol[4,5-*d*]pyridines from a substituted imidazole and acyl or sulfonyl acetonitrile," Tetrahedron, vol. 63(18):3745-3753.

Zhong et al., 2006, "LKB1 mutation in large cell carcinoma of the lung," Cancer Lung, vol. 53(3):285-294.

Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.

Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.

Aparicio et al., 2002, "Review of the clinical experience with 5-azacytidine and 5-aza-2'-deoxycytidine in solid tumors," Current Opinion in Investigational Drugs, Apr. 1, 2002, pp. 627-633, vol. 3, No. 4, Pharmapress, US.

Howard et al., 2011, "Therapeutic targets in head and neck squamous cell carcinoma: Identification, evaluation, and clinical translation," Oral Oncology, Sep. 27, 2011, pp. 10-17, vol. 48, No. 1, Elsevier Science, Oxford, GB.

\* cited by examiner

METHODS FOR TREATING CANCER USING TOR KINASE INHIBITOR COMBINATION THERAPY

This application claims the benefit of U.S. Provisional Application No. 61/813,053, filed Apr. 17, 2013, the entire contents of which are incorporated herein by reference.

1. FIELD

Provided herein are methods for treating or preventing a cancer, comprising administering an effective amount of a TOR kinase inhibitor and an effective amount of a cytidine analog to a patient having a cancer.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for TOR kinase inhibitors that inhibit both mTORC1 and mTORC2 complexes.

DNA-dependent protein kinase (DNA-PK) is a serine/threonine kinase involved in the repair of DNA double strand breaks (DSBs). DSBs are considered to be the most lethal DNA lesion and occur endogenously or in response to ionizing radiation and chemotherapeutics (for review see Jackson, S. P., Bartek, J. The DNA-damage response in human biology and disease. Nature Rev 2009; 461:1071-1078). If left unrepaired, DSBs will lead to cell cycle arrest and/or cell death (Hoeijmakers, J. H. J. Genome maintenance mechanisms for preventing cancer. Nature 2001; 411: 366-374; van Gent, D. C., Hoeijmakers, J. H., Kanaar, R. Chromosomal stability and the DNA double-stranded break connection. *Nat Rev Genet* 2001; 2: 196-206). In response to the insult, cells have developed complex mechanisms to repair such breaks and these mechanisms may form the basis of therapeutic resistance. There are two major pathways used to repair DSBs, non-homologous end joining (NHEJ) and homologous recombination (HR). NHEJ brings broken ends of the DNA together and rejoins them without reference to a second template (Collis, S. J., DeWeese, T. L., Jeggo P. A., Parker, A. R. The life and death of DNA-PK. Oncogene 2005; 24: 949-961). In contrast, HR is dependent on the proximity of the sister chromatid which provides a template to mediate faithful repair (Takata, M., Sasaki, M. S., Sonoda, E., Morrison, C., Hashimoto, M., Utsumi, H., et al. Homologous recombination and non-homologous end joining pathways of DNA double-strand break repair have overlapping roles in the maintenance of chromosomal integrity in vertebrate cells. EMBO J 1998; 17: 5497-5508; Haber, J. E. Partners and pathways repairing a double-strand break. Trends Genet 2000; 16: 259-264). NHEJ repairs the majority of DSBs. In NHEJ, DSBs are recognized by the Ku protein that binds and then activates the catalytic subunit of DNA-PK. This leads to recruitment and activation of end-processing enzymes, polymerases and DNA ligase IV (Collis, S. J., DeWeese, T. L., Jeggo P. A., Parker, A. R. The life and death of DNA-PK. Oncogene 2005; 24: 949-961). NHEJ is primarily controlled by DNA-PK and thus inhibition of DNA-PK is an attractive approach to modulating the repair response to exogenously induced DSBs. Cells deficient in components of the NHEJ pathway are defective in DSB repair and highly sensitive to ionizing radiation and topoisomerase poisons (reviewed by Smith, G. C. M., Jackson, S. P. The DNA-dependent protein kinase. *Genes Dev* 1999; 13: 916-934; Jeggo, P. A., Caldecott, K., Pidsley, S., Banks, G. R. Sensitivity of Chinese hamster ovary mutants defective in DNA double strand break repair to topoisomerase II inhibitors. *Cancer Res* 1989; 49: 7057-7063). A DNA-PK inhibitor has been reported to have the same effect of sensitizing cancer cells to therapeutically induced DSBs (Smith, G. C. M., Jackson, S. P. The DNA-dependent protein kinase. *Genes Dev* 1999; 13: 916-934).

Citation or identification of any reference in Section 2 of this application is not to be construed as an admission that the reference is prior art to the present application.

3. SUMMARY

Provided herein are methods for treating or preventing a cancer, comprising administering an effective amount of a TOR kinase inhibitor and an effective amount of a cytidine analog to a patient having a cancer.

In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with a cytidine analog to said patient. In certain embodiments, provided herein are methods for achieving a National Cancer Institute-Sponsored Working Group on Chronic Lymphocytic Leukemia (NCI-WG CLL) response definition of complete response, partial response or stable disease in a patient having leukemia, comprising administering an effective amount of a TOR kinase inhibitor in combination with a cytidine analog to said patient. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with a cytidine analog to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with a cytidine analog to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with a cytidine analog to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with a cytidine analog to said patient.

In certain embodiments, provided herein are methods for increasing survival without tumor progression of a patient having a cancer, comprising administering an effective amount of a TOR kinase inhibitor in combination with an effective amount of a cytidine analog to said patient.

In certain embodiments, the TOR kinase inhibitor is a compound as described herein.

The present embodiments can be understood more fully by reference to the detailed description and examples, which are intended to exemplify non-limiting embodiments.

4. BRIEF DESCRIPTION OF THE DRAWINGS

FIG. 1 depicts the effects of Compound 1 on HepG2 colony formation. HepG2 cells were plated in agar and incubated with Compound 1 for 8 days before colonies were counted. Data were calculated as the percentage of control relative to the cells treated with DMSO only=100% control. Each data point represents the mean of n=3 experiments in triplicate. ***$p<0.001$ vs DMSO control by one way ANOVA followed by Dunnett's post test.

Figure 2:
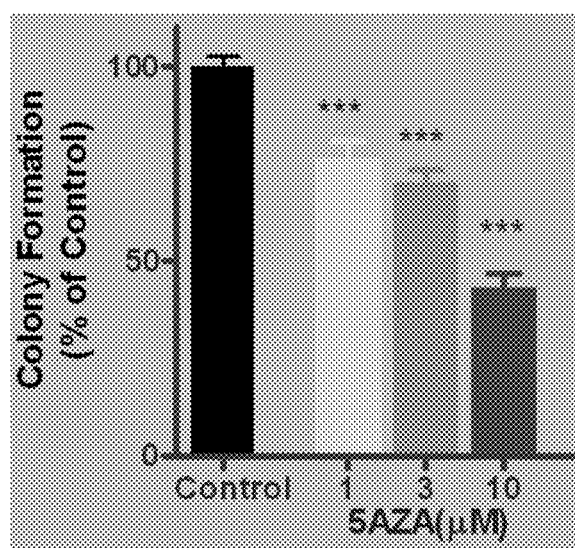

FIG. 2 depicts the effects of 5-AZA on HepG2 colony formation. HepG2 cells were plated in agar and incubated with compound for 8 days before colonies were counted. Data were calculated as the percentage of control relative to the cells treated with DMSO only=100% control. Each data point represents the mean of n=3 experiments in triplicate. ***$p<0.001$.

Figure 3:
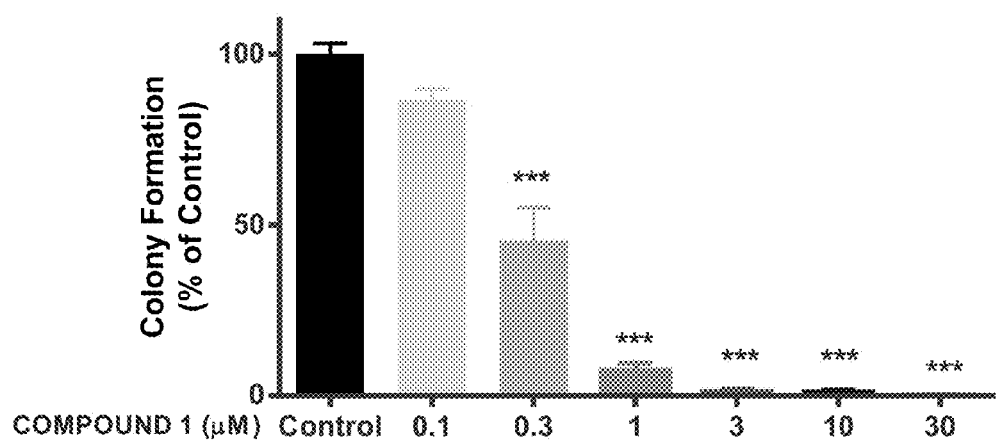

FIG. 3 depicts the effects of Compound 1 on SK-Hep-1 colony formation. SK-HEP-1 cells were plated in agar and incubated with Compound 1 for 8-10 days before colonies were counted. Data were calculated as the percentage of control relative to the cells treated with DMSO only=100% control. Each data point represents the mean of n=3 experiments in triplicate. ***$p<0.001$ vs DMSO control by one way ANOVA followed by Dunnett's post test.

Figure 4:
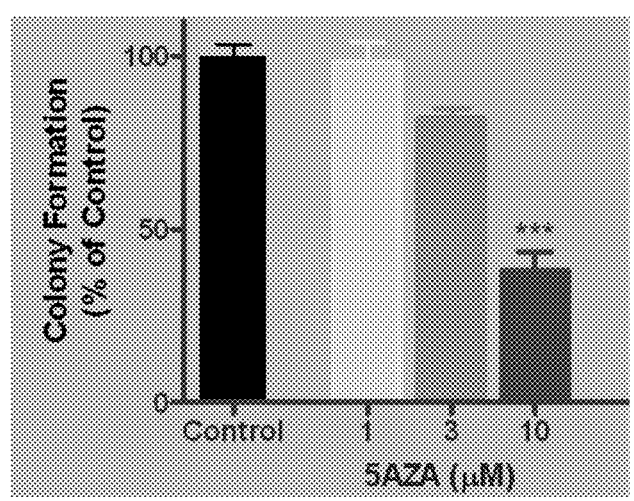

FIG. 4 depicts the effects of 5-AZA on SK-Hep-1 colony formation. SK-HEP-1 cells were plated in agar and incubated with compound for 8 days before colonies were counted. Data were calculated as the percentage of control relative to the cells treated with DMSO only=100% control. Each data point represents the mean of n=3 experiments in triplicate. ***$p<0.001$.

Figure 5:
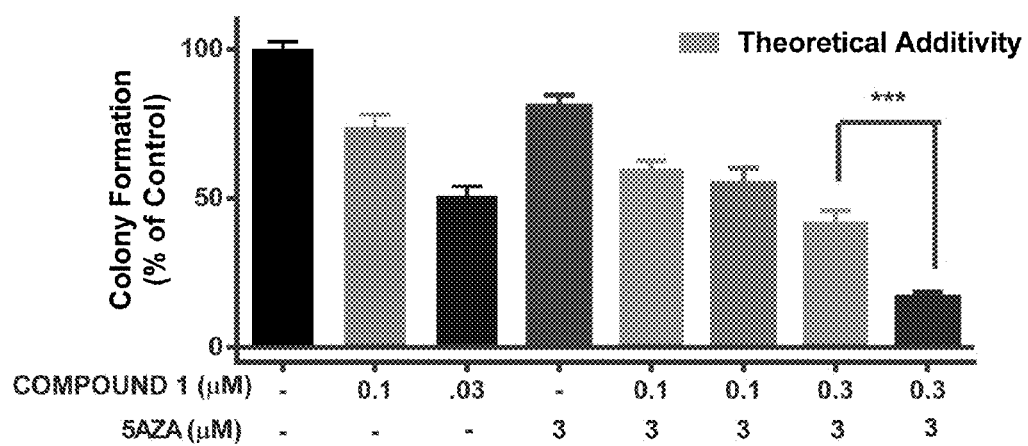

FIG. 5 depicts the effects of Compound 1 plus 5-AZA on HepG2 colony formation. HepG2 cells were plated in agar and incubated with compound for 8 days before colonies were counted. Data were calculated as the percentage of control relative to the cells treated with DMSO only=100% control. Each data point represents the mean of n=3 experiments in triplicate. ***$p<0.001$ vs theoretical additivity by unpaired t test.

Figure 6:
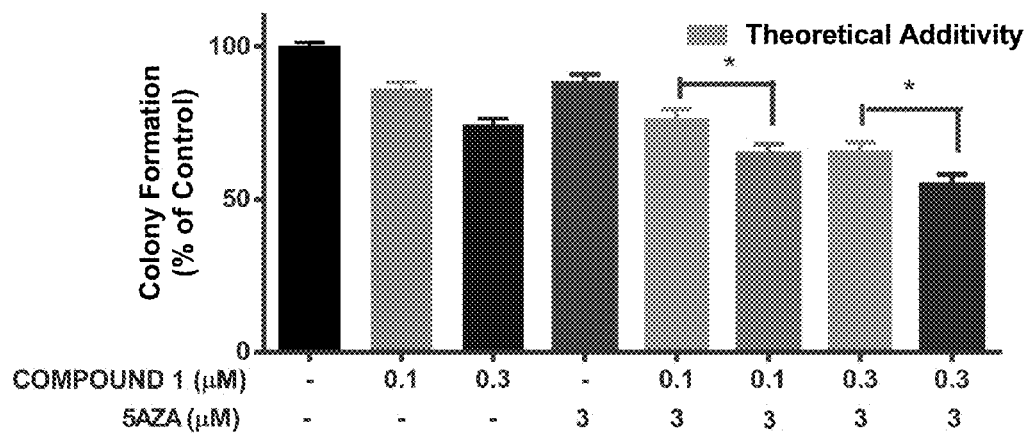

FIG. 6 depicts the effects of Compound 1 plus 5-AZA on SK-Hep-1 colony formation. SK-Hep-1 cells were plated in agar and incubated with compound for 8 days before colonies were counted. Data were calculated as the percentage of control relative to the cells treated with DMSO only=100% control. Each data point represents the mean of n=3 experiments in triplicate. *p<0.05 vs theoretical additivity by unpaired t test.

5. DETAILED DESCRIPTION

5.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxyl amine" group is a radical of the formula: —N(R$^\#$)OH or —NHOH, wherein R$^\#$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N(R$^\#$)O-alkyl or —NHO-alkyl, wherein R$^\#$ is as defined above.

An "aralkoxyamine" group is a radical of the formula: —N(R$^\#$)O-aryl or —NHO-aryl, wherein R$^\#$ is as defined above.

An "alkylamine" group is a radical of the formula: —NH-alkyl or N(alkyl)$_2$, wherein each alkyl is independently as defined above.

An "aminocarbonyl" group is a radical of the formula: —C(=O)N(R$^\#$)$_2$, —C(=O)NH(R$^\#$) or —C(=O)NH$_2$, wherein each R$^\#$ is as defined above.

An "acylamino" group is a radical of the formula: —NHC(=O)(R$^\#$) or —)C(=O)(R$^\#$), wherein each alkyl and R$^\#$ are independently as defined above.

An "O(alkyl)aminocarbonyl" group is a radical of the formula: —O(alkyl)C(=O)N(R$^\#$)$_2$, —O(alkyl)C(=O)NH(R$^\#$) or —O(alkyl)C(=O)NH$_2$, wherein each R$^\#$ is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R$^\#$), wherein R$^\#$ is as defined above.

An "aldehyde" group is a radical of the formula: —CH(=O).

An "ester" group is a radical of the formula: —C(=O)O(R$^\#$) or —OC(=O)(R$^\#$), wherein R$^\#$ is as defined above.

A "urea" group is a radical of the formula: —N(alkyl)C(=O)N(R$^\#$)$_2$, —N(alkyl)C(=O)NH(R$^\#$), —)C(=O)NH$_2$, —NHC(=O)N(R$^\#$)$_2$, —NHC(=O)NH(R$^\#$), or —NHC(=O)NH$_2^\#$, wherein each alkyl and R$^\#$ are independently as defined above.

An "imine" group is a radical of the formula: —N=C(R$^\#$)$_2$ or —C(R$^\#$)=N(R$^\#$), wherein each R$^\#$ is independently as defined above.

An "imide" group is a radical of the formula: —C(=O)N(R#)C(=O)(R$^\#$) or —N((C=O)(R$^\#$)$_2$, wherein each R$^\#$ is independently as defined above.

A "urethane" group is a radical of the formula: —OC(=O)N(R$^\#$)$_2$, —OC(=O)NH(R$^\#$), —N(R$^\#$)C(=O)O(R$^\#$), or —NHC(=O)O(R$^\#$), wherein each R$^\#$ is independently as defined above.

An "amidine" group is a radical of the formula: —C(=N(R$^\#$))N(R$^\#$)$_2$, —C(=N(R$^\#$))NH(R$^\#$), —C(=N(R$^\#$))NH$_2$, —C(=NH)N(R$^\#$)$_2$, —C(=NH)NH(R$^\#$), —C(=NH)NH$_2$, —N=C(R$^\#$)N(R$^\#$)$_2$, —N=C(R$^\#$)NH(R$^\#$), —N=C(R$^\#$)NH$_2$, —N(R$^\#$)C(R$^\#$)=N(R$^\#$), —NHC(R$^\#$)=N(R$^\#$), —N(R$^\#$)C(R$^\#$)=NH, or —NHC(R$^\#$)=NH, wherein each R$^\#$ is independently as defined above.

A "guanidine" group is a radical of the formula: —N(R$^\#$)C(=N(R$^\#$))N(R$^\#$)$_2$, —NHC(=N(R$^\#$))N(R$^\#$)$_2$, —N(R$^\#$)C(=NH)N(R$^\#$)$_2$, —N(R$^\#$)C(=N(R$^\#$))NH(R$^\#$), —N(R$^\#$)C(=N(R$^\#$))NH$_2$, —NHC(=NH)N(R$^\#$)$_2$, —NHC(=N(R$^\#$))NH(R$^\#$), —NHC(=N(R$^\#$))NH$_2$, —NHC(=NH)NH(R$^\#$), —NHC(=NH)NH$_2$, —N=C(N(R$^\#$)$_2$)$_2$, —N=C(NH(R$^\#$))$_2$, or —N=C(NH$_2$)$_2$, wherein each R$^\#$ is independently as defined above.

A "enamine" group is a radical of the formula: —N(R$^\#$)C(R$^\#$)=C(R$^\#$)$_2$, —NHC(R$^\#$)=C(R$^\#$)$_2$, —C(N(R$^\#$)$_2$)=C(R$^\#$)$_2$, —C(NH(R$^\#$))=C(R$^\#$)$_2$, —C(NH$_2$)=C(R$^\#$)$_2$, —C(R$^\#$)=C(R$^\#$)(N(R$^\#$)$_2$), —C(R$^\#$)=C(R$^\#$)(NH(R$^\#$)) or —C(R$^\#$)=C(R$^\#$)(NH$_2$), wherein each R$^\#$ is independently as defined above.

An "oxime" group is a radical of the formula: —C(=NO(R$^\#$))(R$^\#$), —C(=NOH)(R$^\#$), —CH(=NO(R$^\#$)), or —CH(=NOH), wherein each R$^\#$ is independently as defined above.

A "hydrazide" group is a radical of the formula: —C(=O)N(R$^\#$)N(R$^\#$)$_2$, —C(=O)NHN(R$^\#$)$_2$, —C(=O)N ($R^\#$)NH($R^\#$), —C(=O)N($R^\#$)NH$_2$, —C(=O)NHNH($R^\#$)$_2$, or —C(=O)NHNH$_2$, wherein each $R^\#$ is independently as defined above.

A "hydrazine" group is a radical of the formula: —N($R^\#$)N($R^\#$)$_2$, —NHN($R^\#$)$_2$, —N($R^\#$)NH($R^\#$), —N($R^\#$)NH$_2$, —NHNH($R^\#$)$_2$, or —NHNH$_2$, wherein each $R^\#$ is independently as defined above.

A "hydrazone" group is a radical of the formula: —C(=N—N($R^\#$)$_2$)($R^\#$)$_2$, —C(=N—NH($R^\#$))($R^\#$)$_2$, —C(=N—NH$_2$)($R^\#$)$_2$, —N($R^\#$)(N=C($R^\#$)$_2$), or —NH(N=C($R^\#$)$_2$), wherein each $R^\#$ is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S($R^\#$), wherein $R^\#$ is as defined above.

A "thiocarbonyl" group is a radical of the formula: —C(=S)($R^\#$), wherein $R^\#$ is as defined above.

A "sulfinyl" group is a radical of the formula: —S(=O)($R^\#$), wherein $R^\#$ is as defined above.

A "sulfone" group is a radical of the formula: —S(=O)$_2$($R^\#$), wherein $R^\#$ is as defined above.

A "sulfonylamino" group is a radical of the formula: —NHSO$_2$($R^\#$) or —N(alkyl)SO$_2$($R^\#$), wherein each alkyl and $R^\#$ are defined above.

A "sulfonamide" group is a radical of the formula: —S(=O)$_2$N($R^\#$)$_2$, or —S(=O)$_2$NH($R^\#$), or —S(=O)$_2$NH$_2$, wherein each $R^\#$ is independently as defined above.

A "phosphonate" group is a radical of the formula: —P(=O)(O($R^\#$))$_2$, —P(=O)(OH)$_2$, —OP(=O)(O($R^\#$))($R^\#$), or —OP(=O)(OH)($R^\#$), wherein each $R^\#$ is independently as defined above.

A "phosphine" group is a radical of the formula: —P($R^\#$)$_2$, wherein each $R^\#$ is independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the TOR kinase inhibitors include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a TOR kinase inhibitor, or a salt thereof, in the form of a crystal lattice that contains spaces (e.g., channels) that have a guest molecule (e.g., a solvent or water) trapped within or a crystal lattice wherein a TOR kinase inhibitor is a guest molecule.

As used herein and unless otherwise indicated, the term "solvate" means a TOR kinase inhibitor, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a TOR kinase inhibitor, or a salt thereof, that further includes a stoichiometric or non-stoichiometric amount of water bound by non-covalent intermolecular forces.

As used herein and unless otherwise indicated, the term "prodrug" means a TOR kinase inhibitor derivative that can hydrolyze, oxidize, or otherwise react under biological conditions (in vitro or in vivo) to provide an active compound, particularly a TOR kinase inhibitor. Examples of prodrugs include, but are not limited to, derivatives and metabolites of a TOR kinase inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a TOR kinase inhibitor that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The TOR kinase inhibitors can have chiral centers and can occur as racemates, individual enantiomers or diastereomers, and mixtures thereof. All such isomeric forms are included within the embodiments disclosed herein, including mixtures thereof. The use of stereomerically pure forms of such TOR kinase inhibitors, as well as the use of mixtures of those forms are encompassed by the embodiments disclosed herein. For example, mixtures comprising equal or unequal amounts of the enantiomers of a particular TOR kinase inhibitor may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the TOR kinase inhibitors can include E and Z isomers, or a mixture thereof, and cis and trans isomers or a mixture thereof. In certain embodiments, the TOR kinase inhibitors are isolated as either the cis or trans isomer. In other embodiments, the TOR kinase inhibitors are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

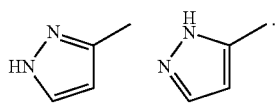

As readily understood by one skilled in the art, a wide variety of functional groups and other structures may exhibit tautomerism and all tautomers of the TOR kinase inhibitors are within the scope of the present invention.

It should also be noted the TOR kinase inhibitors can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically encriched compounds are useful as therapeutic agents, e.g., cancer and inflammation therapeutic agents, research reagents, e.g., binding assay reagents, and diagnostic agents, e.g., in vivo imaging agents. All isotopic variations of the TOR kinase inhibitors as described herein, whether radioactive or not, are intended to be encompassed within the scope of the embodiments provided herein. In some embodiments, there are provided isotopologues of the TOR kinase inhibitors, for example, the isotopologues are deuterium, carbon-13, or nitrogen-15 enriched TOR kinase inhibitors.

It should be noted that if there is a discrepancy between a depicted structure and a name for that structure, the depicted structure is to be accorded more weight.

"Treating" as used herein, means an alleviation, in whole or in part, of a cancer or a symptom associated with a cancer, or slowing, or halting of further progression or worsening of those symptoms.

"Preventing" as used herein, means the prevention of the onset, recurrence or spread, in whole or in part, of a cancer, or a symptom thereof.

The term "effective amount" in connection with an TOR kinase inhibitor or a cytidine analog means an amount alone or in combination capable of alleviating, in whole or in part, a symptom associated with a cancer, or slowing or halting further progression or worsening of those symptoms, or treating or preventing a cancer in a subject having or at risk for having a cancer. The effective amount of the TOR kinase inhibitor or a cytidine analog, for example in a pharmaceutical composition, may be at a level that will exercise the desired effect; for example, about 0.005 mg/kg of a subject's body weight to about 100 mg/kg of a patient's body weight in unit dosage for both oral and parenteral administration.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

As used herein, and unless otherwise specified, the term "in combination with" includes the administration of two or more therapeutic agents simultaneously, concurrently, or sequentially within no specific time limits unless otherwise indicated. In one embodiment, a TOR kinase inhibitor is administered in combination with a cytidine analog. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, or any combination thereof. For example, in one embodiment, the first agent can be administered prior to the second therapeutic agent, for e.g. 1 week. In another, the first agent can be administered prior to (for example 1 day prior) and then concomitant with the second therapeutic agent.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having a cancer.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident advanced cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or | | |

-continued

| Response | Definition | Nodal Masses | Spleen, liver | Bone Marrow |
|---|---|---|---|---|
| PD or relapsed disease | Any new lesion or increase by ≥50% of previously involved sites from nadir | PET negative; no change in size of previous lesions on CT Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |

| Parameter | CR | PR | PD |
|---|---|---|---|
| Splenomegaly | None | Decrease ≥50% | Increase ≥50% |
| Blood lymphocytes | <4000/μL | Decrease ≥50% from baseline | Increase ≥50% over baseline |
| Marrow‡ | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils‡ | >1500/μL | >1500/μL or >50% improvement over baseline | |

A criteria define the tumor load;
Group B criteria define the function of the hematopoietic system (or marrow).
CR (complete remission): all of the criteria have to be met, and patients have to lack disease-related constitutional symptoms;
PR (partial remission): at least two of the criteria of group A plus one of the criteria of group B have to be met;
SD is absence of progressive disease (PD) and failure to achieve at least a PR;
PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;

-continued

| Response Subcategory | Response Criteria[a] |
|---|---|

FLC, free light chain;
PR, partial response;
SD, stable disease;
sCR, stringent complete response;
VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK 52056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

5.2 TOR Kinase Inhibitors

The compounds provided herein are generally referred to as "TOR kinase inhibitor(s)." In one aspect, the TOR kinase inhibitors do not include rapamycin or rapamycin analogs (rapalogs).

In one embodiment, the TOR kinase inhibitors include compounds having the following formula (I):

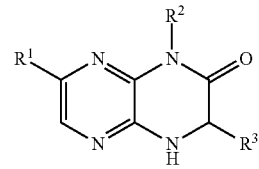

and pharmaceutically acceptable salts, clathrates, solvates, stereoisomers, tautomers, metabolites, isotopologues and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the TOR kinase inhibitors do not include 7-(4-hydroxyphenyl)-1-(3-methoxybenzyl)-3,4-dihydropyrazino[2,3-b]pyrazin-2(1H)-one, depicted below:

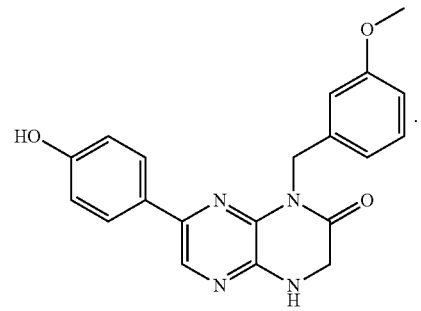 [SMILES: COc1cccc(CN2C(=O)CNc3ncc(-c4ccc(O)cc4)nc32)c1]

In some embodiments of compounds of formula (I), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —NR$_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —NR$_2$, wherein R is independently H, or a substituted or unsubstituted $C_{1-4}$ alkyl.

In some embodiments, $R^1$ is

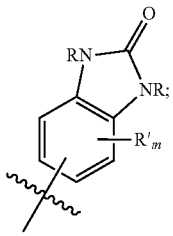

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —NR$_2$; m is 0-3; and n is 0-3. It will be understood by those skilled in the art that any of the substituents R' may be attached to any suitable atom of any of the rings in the fused ring systems.

In some embodiments of compounds of formula (I), $R^1$ is

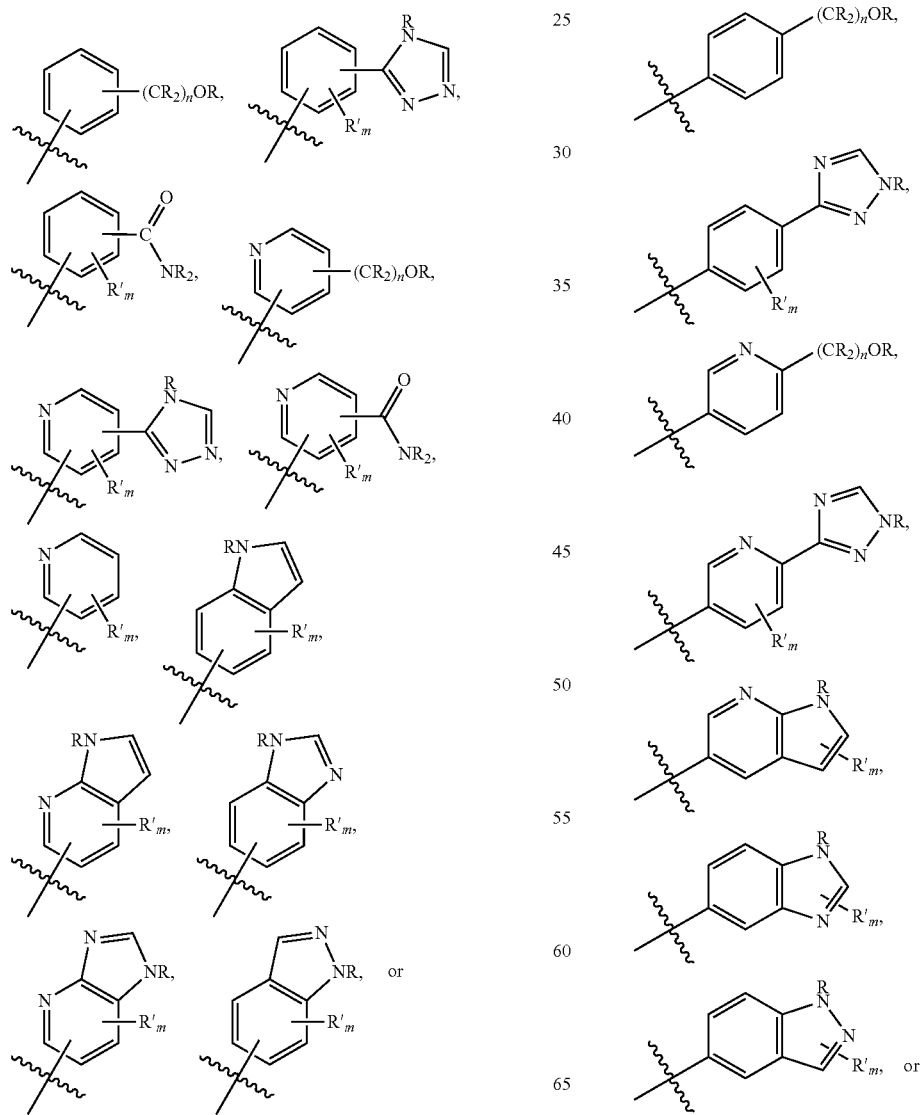

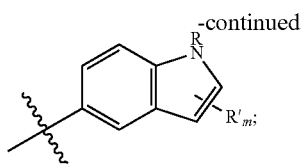

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —NR$_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

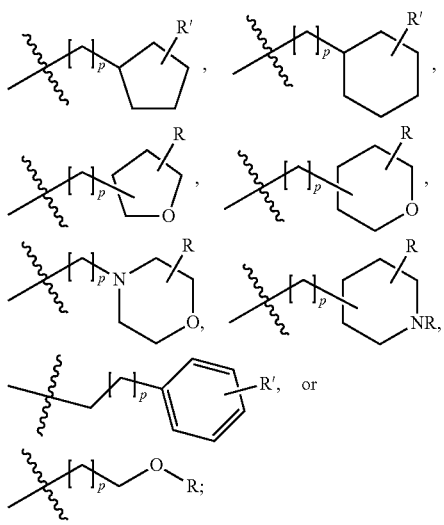

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (I), $R^2$ is H, $C_{1-4}$ alkyl, ($C_{1-4}$alkyl)(OR),

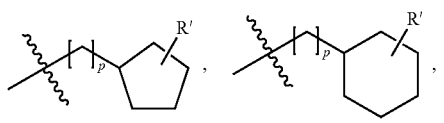

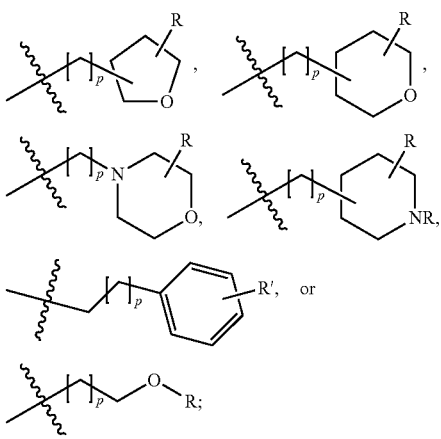

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (I), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —NR$_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —NR$_2$, wherein R is independently H, or a substituted or unsubstituted $C_{1-4}$ alkyl.

In certain embodiments, the compounds of formula (I) have an $R^1$ group set forth herein and an $R^2$ group set forth herein.

In some embodiments of compounds of formula (I), the compound inhibits TOR kinase. In other embodiments of compounds of formula (I), the compound inhibits DNA-PK. In certain embodiments of compounds of formula (I), the compound inhibits both TOR kinase and DNA-PK In some embodiments of compounds of formula (I), the compound at a concentration of 10 μM inhibits mTOR kinase, DNA-PK, PI3K, or a combination thereof by at least about 50%. Compounds of formula (I) may be shown to be inhibitors of the kinases above in any suitable assay system.

Representative TOR kinase inhibitors of formula (I) include compounds from Table A.

TABLE A 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-methoxycyclohexyl)-3,4-dihydropyrazino[2,3-b]pyrazin-2(1H)-one;
7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;
1-ethyl-7-(1H-pyrrolo[3,2-b]pyridin-5-yl)-3,4-dihydropyrazino[2,3-b]pyrazin-2(1H)-one;
7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;
7-(1H-benzo[d]imidazol-4-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;
7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;
7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;
7-(6-(1H-1,2,4-triazol-3-yl)pyridin-3-yl)-1-(2-methoxyethyl)-3,4-dihydropyrazino[2,3-b]pyrazin-2(1H)-one;
7-(6-(1H-1,2,4-triazol-3-yl)pyridin-3-yl)-1-ethyl-3,4-dihydropyrazino[2,3-b]pyrazin-2(1H)-one;
7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;
7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;
7-(1H-indol-4-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(trans-4-hydroxycyclohexyl)-3,4-dihydropyrazino[2,3-b]pyrazin-2(1H)-one;
7-(6-(1H-1,2,4-triazol-3-yl)pyridin-3-yl)-1-(trans-4-methoxycyclohexyl)-3,4-dihydropyrazino[2,3-b]pyrazin-2(1H)-one;
7-(6-(1H-1,2,4-triazol-3-yl)pyridin-3-yl)-1-isopropyl-3,4-dihydropyrazino[2,3-b]pyrazin-2(1H)-one;
7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;
7-(5-fluoro-2-methyl-4-(1H-1,2,4-triazol-3-yl)phenyl)-1-isopropyl-3,4-dihydropyrazino[2,3-b]pyrazin-2(1H)-one;
1-ethyl-7-(5-fluoro-2-methyl-4-(1H-1,2,4-triazol-3-yl)phenyl)-3,4-dihydropyrazino[2,3-b]pyrazin-2(1H)-one;
7-(2-hydroxypyridin-4-yl)-1-(2-(tetrahydro-2H-pyran-4-yl)ethyl)-3,4-dihydropyrazino[2,3-b]pyrazin-2(1H)-one;
1-isopropyl-7-(4-methyl-6-(1H-1,2,4-triazol-3-yl)pyridin-3-yl)-3,4-dihydropyrazino[2,3-b]pyrazin-2(1H)-one;
5-(8-isopropyl-7-oxo-5,6,7,8-tetrahydropyrazino[2,3-b]pyrazin-2-yl)-4-methylpicolinamide;
7-(1H-indazol-4-yl)-1-(2-(tetrahydro-2H-pyran-4-yl)ethyl)-3,4-dihydropyrazino[2,3-b]pyrazin-2(1H)-one;
7-(2-aminopyrimidin-5-yl)-1-(2-(tetrahydro-2H-pyran-4-yl)ethyl)-3,4-dihydropyrazino[2,3-b]pyrazin-2(1H)-one;
7-(2-aminopyridin-4-yl)-1-(2-(tetrahydro-2H-pyran-4-yl)ethyl)-3,4-dihydropyrazino[2,3-b]pyrazin-2(1H)-one;
7-(6-(methylamino)pyridin-3-yl)-1-(2-(tetrahydro-2H-pyran-4-yl)ethyl)-3,4-dihydropyrazino[2,3-b]pyrazin-2(1H)-one;
7-(6-hydroxypyridin-3-yl)-1-(2-(tetrahydro-2H-pyran-4-yl)ethyl)-3,4-dihydropyrazino[2,3-b]pyrazin-2(1H)-one;
7-(4-(1H-pyrazol-3-yl)phenyl)-1-(2-methoxyethyl)-3,4-dihydropyrazino[2,3-b]pyrazin-2(1H)-one;
7-(pyridin-3-yl)-1-(2-(tetrahydro-2H-pyran-4-yl)ethyl)-3,4-dihydropyrazino[2,3-b]pyrazin-2(1H)-one;
7-(1H-indazol-4-yl)-1-(2-methoxyethyl)-3,4-dihydropyrazino[2,3-b]pyrazin-2(1H)-one;
7-(1H-indazol-6-yl)-1-(2-methoxyethyl)-3,4-dihydropyrazino[2,3-b]pyrazin-2(1H)-one;
7-(pyrimidin-5-yl)-1-(2-(tetrahydro-2H-pyran-4-yl)ethyl)-3,4-dihydropyrazino[2,3-b]pyrazin-2(1H)-one;
7-(6-methoxypyridin-3-yl)-1-(2-(tetrahydro-2H-pyran-4-yl)ethyl)-3,4-dihydropyrazino[2,3-b]pyrazin-2(1H)-one;

TABLE A-continued 1-(2-methoxyethyl)-7-(1H-pyrrolo[2,3-b]pyridin-5-yl)-3,4-dihydropyrazino[2,3-b]pyrazin-2(1H)-one;
1-ethyl-7-(1H-pyrrolo[2,3-b]pyridin-5-yl)-3,4-dihydropyrazino[2,3-b]pyrazin-2(1H)-one;
1-ethyl-7-(1H-indazol-4-yl)-3,4-dihydropyrazino[2,3-b]pyrazin-2(1H)-one;
7-(pyridin-4-yl)-1-(2-(tetrahydro-2H-pyran-4-yl)ethyl)-3,4-dihydropyrazino[2,3-b]pyrazin-2(1H)-one;
7-(6-aminopyridin-3-yl)-1-(2-(tetrahydro-2H-pyran-4-yl)ethyl)-3,4-dihydropyrazino[2,3-b]pyrazin-2(1H)-one;
1-methyl-7-(2-methyl-6-(4H-1,2,4-triazol-3-yl)pyridin-3-yl)-3,4-dihydropyrazino[2,3-b]pyrazin-2(1H)-one;
2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;
4-methyl-5-(7-oxo-8-((tetrahydro-2H-pyran-4-yl)methyl)-5,6,7,8-tetrahydropyrazino[2,3-b]pyrazin-2-yl)picolinamide;
5-(8-((cis-4-methoxycyclohexyl)methyl)-7-oxo-5,6,7,8-tetrahydropyrazino[2,3-b]pyrazin-2-yl)-4-methylpicolinamide;
7-(1H-pyrazol-4-yl)-1-(2-(tetrahydro-2H-pyran-4-yl)ethyl)-3,4-dihydropyrazino[2,3-b]pyrazin-2(1H)-one;
1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;
3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;
1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;
3-(7-oxo-8-(2-(tetrahydro-2H-pyran-4-yl)ethyl)-5,6,7,8-tetrahydropyrazino[2,3-b]pyrazin-2-yl)benzamide;
5-(8-((trans-4-methoxycyclohexyl)methyl)-7-oxo-5,6,7,8-tetrahydropyrazino[2,3-b]pyrazin-2-yl)-4-methylpicolinamide;
3-((7-(6-(2-hydroxypropan-2-yl)pyridin-3-yl)-2-oxo-3,4-dihydropyrazino[2,3-b]pyrazin-1(2H)-yl)methyl)benzonitrile;
7-(6-(2-hydroxypropan-2-yl)pyridin-3-yl)-1-((1R,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3S)-3-methoxycyclopentyl)-3,4-dihydropyrazino[2,3-b]pyrazin-2(1H)-one;
7-(6-(2-hydroxypropan-2-yl)pyridin-3-yl)-1-((1R,3S)-3-methoxycyclopentyl)-3,4-dihydropyrazino[2,3-b]pyrazin-2(1H)-one;
7-(1H-indazol-6-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(2-morpholinoethyl)-3,4-dihydropyrazino[2,3-b]pyrazin-2(1H)-one;
1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(2-morpholinoethyl)-3,4-dihydropyrazino[2,3-b]pyrazin-2(1H)-one;
1-isopropyl-7-(2-methyl-6-(4H-1,2,4-triazol-3-yl)pyridin-3-yl)-3,4-dihydropyrazino[2,3-b]pyrazin-2(1H)-one;
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
1-(trans-4-hydroxycyclohexyl)-7-(6-(2-hydroxypropan-2-yl)pyridin-3-yl)-3,4-dihydropyrazino[2,3-b]pyrazin-2(1H)-one;
1-(cis-4-hydroxycyclohexyl)-7-(6-(2-hydroxypropan-2-yl)pyridin-3-yl)-3,4-dihydropyrazino[2,3-b]pyrazin-2(1H)-one;
4-(7-oxo-8-(2-(tetrahydro-2H-pyran-4-yl)ethyl)-5,6,7,8-tetrahydropyrazino[2,3-b]pyrazin-2-yl)benzamide;
7-(1H-indazol-5-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
7-(1H-indol-5-yl)-1-(2-(tetrahydro-2H-pyran-4-yl)ethyl)-3,4-dihydropyrazino[2,3-b]pyrazin-2(1H)-one;
1-ethyl-7-(2-methyl-6-(4H-1,2,4-triazol-3-yl)pyridin-3-yl)-3,4-dihydropyrazino[2,3-b]pyrazin-2(1H)-one;
7-(1H-indol-6-yl)-1-(2-(tetrahydro-2H-pyran-4-yl)ethyl)-3,4-dihydropyrazino[2,3-b]pyrazin-2(1H)-one;

TABLE A-continued 7-(4-(2-hydroxypropan-2-yl)phenyl)-1-(trans-4-methoxycyclohexyl)-3,4-dihydropyrazino[2,3-b]pyrazin-2(1H)-one;
7-(6-(2-hydroxypropan-2-yl)pyridin-3-yl)-1-(tetrahydro-2H-pyran-4-yl)-3,4-dihydropyrazino[2,3-b]pyrazin-2(1H)-one;
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((cis-4-methoxycyclohexyl)methyl)-3,4-dihydropyrazino[2,3-b]pyrazin-2(1H)-one;
1-(2-methoxyethyl)-7-(4-methyl-2-(methylamino)-1H-benzo[d]imidazol-6-yl)-3,4-dihydropyrazino[2,3-b]pyrazin-2(1H)-one;
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;
7-(2-methyl-4-(4H-1,2,4-triazol-3-yl)phenyl)-3,4-dihydropyrazino[2,3-b]pyrazin-2(1H)-one;
1-(2-methoxyethyl)-7-(4-methyl-6-(1H-1,2,4-triazol-3-yl)pyridin-3-yl)-3,4-dihydropyrazino[2,3-b]pyrazin-2(1H)-one;
1-benzyl-7-(2-methyl-4-(4H-1,2,4-triazol-3-yl)phenyl)-3,4-dihydropyrazino[2,3-b]pyrazin-2(1H)-one;
7-(3-fluoro-4-(4H-1,2,4-triazol-3-yl)phenyl)-1-(2-methoxyethyl)-3,4-dihydropyrazino[2,3-b]pyrazin-2(1H)-one;
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(trans-4-methoxycyclohexyl)-3,4-dihydropyrazino[2,3-b]pyrazin-2(1H)-one;
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
1-(2-methoxyethyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((trans-4-methoxycyclohexyl)methyl)-3,4-dihydropyrazino[2,3-b]pyrazin-2(1H)-one;
1-(cyclopentylmethyl)-7-(6-(2-hydroxypropan-2-yl)pyridin-3-yl)-3,4-dihydropyrazino[2,3-b]pyrazin-2(1H)-one;
7-(4-(2-hydroxypropan-2-yl)phenyl)-1-(2-methoxyethyl)-3,4-dihydropyrazino[2,3-b]pyrazin-2(1H)-one;
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(4-(trifluoromethyl)benzyl)-3,4-dihydropyrazino[2,3-b]pyrazin-2(1H)-one;
7-(6-(2-hydroxypropan-2-yl)pyridin-3-yl)-1-(3-(trifluoromethyl)benzyl)-3,4-dihydropyrazino[2,3-b]pyrazin-2(1H)-one;
7-(6-(2-hydroxypropan-2-yl)pyridin-3-yl)-1-(3-methoxypropyl)-3,4-dihydropyrazino[2,3-b]pyrazin-2(1H)-one;
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-methoxyethyl)-3,4-dihydropyrazino[2,3-b]pyrazin-2(1H)-one;
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;
7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;
7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;
7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;
1-(1-hydroxypropan-2-yl)-7-(2-methyl-6-(1H-1,2,4-triazol-3-yl)pyridin-3-yl)-3,4-

TABLE A-continued dihydropyrazino[2,3-b]pyrazin-2(1H)-one; and
1-(2-hydroxyethyl)-7-(2-methyl-6-(1H-1,2,4-triazol-3-yl)pyridin-3-yl)-3,4-dihydropyrazino[2,3-b]pyrazin-2(1H)-one,
and pharmaceutically acceptable salts, clathrates, solvates, stereoisomers, tautomers, metabolites, isotopologues and prodrugs thereof.

5.3 Cytidine Analogs

Nucleoside analogs have been used clinically for the treatment of viral infections and certain cancers. Most nucleoside analogs are classified as anti-metabolites. After they enter the cell, nucleoside analogs are successively phosphorylated to nucleoside 5'-mono-phosphates, di-phosphates, and tri-phosphates.

The nucleoside analogs 5-azacytidine (also known as 4-amino-1-β-D-ribofuranosyl-1,3,5-triazin-2(1H)-one; National Service Center designation NSC-102816; CAS Registry Number 320-67-2; azacitidine; Aza, AZA and 5-AZA; and currently marketed as VIDAZA®) and 2'-deoxy-5-azacytidine (also known as 5-aza-2'-deoxycytidine, decitabine, 5-aza-CdR, Dac, and DAC, and currently marketed as DACOGEN®) are DNA methyltransferase (DNMT) inhibitors that have been approved by the U.S. Food and Drug Administration for the treatment of myelodysplastic syndromes (MDS). Azacitidine and decitabine are cytidine analogs; a structural difference between these cytidine analogs and their related natural nucleosides is the presence of a nitrogen at position 5 of the cytosine ring in place of a carbon. Azacitidine may be defined as having a molecular formula of $C_8H_{12}N_4O_5$, a molecular weight of 244.21 grams per mole, and a structure as shown below. Decitabine may be defined as having a molecular formula of $C_8H_{12}N_4O_4$, a molecular weight of 228.21 grams per mole, and a structure as shown below.

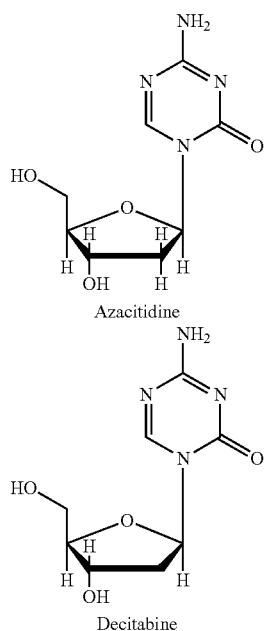

Azacitidine

Decitabine

After its incorporation into replicating DNA, 5-azacytidine or 5-aza-2'-deoxycytidine can form a covalent complex with DNA methyltransferases. DNA methyltransferases are responsible for de novo DNA methylation and for reproducing established methylation patterns in daughter DNA strands of replicating DNA. Inhibition of DNA methyltransferases can lead to DNA hypomethylation, thereby restoring normal functions to morphologically dysplastic, immature cells by re-expression of genes involved in normal cell cycle regulation, differentiation and death. The cytotoxic effects of cytidine analogs can cause the death of rapidly dividing cells that are no longer responsive to normal cell growth control mechanisms. 5-Azacytidine, unlike 5-aza-2'-deoxycytidine, also incorporates into RNA. The cytotoxic effects of azacitidine may result from multiple mechanisms, including inhibition of DNA, RNA and protein synthesis, incorporation into RNA and DNA, and activation of DNA damage pathways.

5-Azacytidine and 5-aza-2'-deoxycytidine have been tested in clinical trials and showed significant activity, such as, for example, in the treatment of myelodysplastic syndromes (MDS), acute myelogenous leukemia (AML), chronic myelogenous leukemia (CML), acute lymphocytic leukemia (ALL), and non Hodgkin's lymphoma (NHL). See, e.g., Aparicio et al., Curr. Opin. Invest. Drugs 3(4): 627-33 (2002). 5-Azacytidine has undergone NCI-sponsored trials for the treatment of MDS and has been approved for treating all FAB subtypes of MDS. See, e.g., Kornblith et al., J. Clin. Oncol. 20(10): 2441-2452 (2002); Silverman et al., J. Clin. Oncol. 20(10): 2429-2440 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., Lancet Oncol., 2009, 10(3):223-32; Silverman et al., Blood 106(11): Abstract 2526 (2005).

Other members of the class of cytidine analogs include, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; and elaidic acid cytarabine.

5-Azacytidine and certain other cytidine analogs are approved for subcutaneous (SC) or intravenous (IV) administration to treat certain proliferative disorders. Oral dosing of cytidine analogs would be more desirable and convenient for patients and doctors, e.g., by eliminating injection-site reactions that may occur with SC administration and/or by permitting improved patient compliance. However, oral delivery of cytidine analogs has proven difficult due to combinations of chemical instability, enzymatic instability, and/or poor permeability. For example, cytidine analogs have been considered acid labile and unstable in the acidic gastric environment. Previous attempts to develop oral dosage forms of cytidine analogs have required enteric coating of the drug core to protect the active pharmaceutical ingredient (API) from what was understood and accepted to be therapeutically unacceptable hydrolysis in the stomach, such that the drug is preferably absorbed in specific regions of the lower gastrointestinal tract, such as the jejunum in the small intestine. See, e.g., Sands, et al., U.S. Patent Publication No. 2004/0162263 (U.S. application Ser. No. 10/698,983). In addition, a generally accepted belief in the art has been that water leads to detrimental hydrolytic degradation of cytidine analogs during formulation, subsequently affecting the stability of the API in the dosage form. As a result, coatings applied to the drug core for prospective oral delivery of cytidine analogs have previously been limited to organic solvent-based systems to minimize exposure of the API to water.

In certain embodiments, the cytidine analog is 5-azacytidine. In other embodiments, the cytidine analog is 5-aza-2'-deoxycytidine (decitabine or 5-aza-CdR). In yet other embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; elaidic acid cytarabine; or their derivatives or related analogs.

In certain embodiments, exemplary cytidine analogs have the structures provided below:

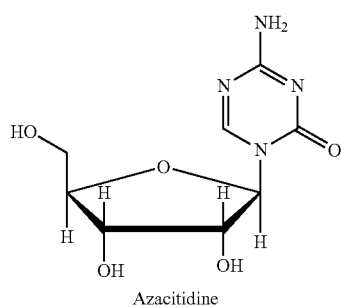

Azacitidine

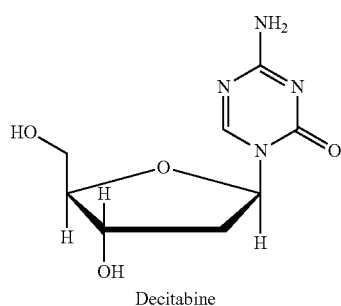

Decitabine

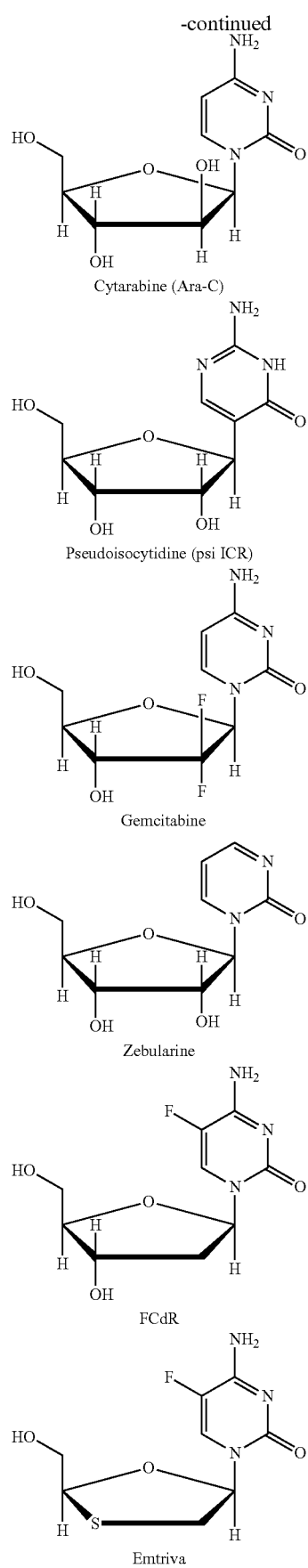

Cytarabine (Ara-C)

Pseudoisocytidine (psi ICR)

Gemcitabine

Zebularine

FCdR

Emtriva

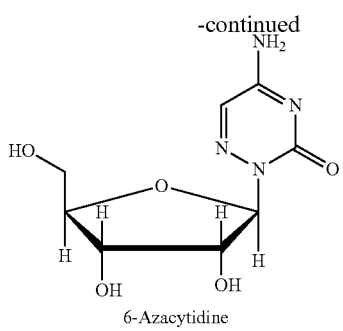

6-Azacytidine

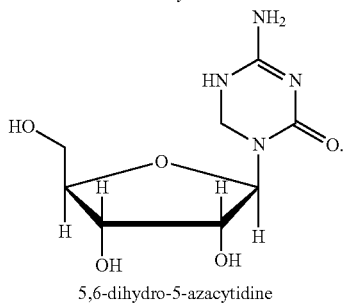

5,6-dihydro-5-azacytidine

5.4 Methods for Making TOR Kinase Inhibitors

The TOR kinase inhibitors can be obtained via standard, well-known synthetic methodology, see e.g., March, J. Advanced Organic Chemistry; Reactions Mechanisms, and Structure, 4th ed., 1992. Starting materials useful for preparing compounds of formula (III) and intermediates therefore, are commercially available or can be prepared from commercially available materials using known synthetic methods and reagents.

Particular methods for preparing compounds of formula (I) are disclosed in U.S. Pat. No. 8,110,578, issued Feb. 7, 2012, and U.S. Pat. No. 8,569,494, issued Oct. 29, 2013, each incorporated by reference herein in their entirety.

5.5 Methods of Use

Provided herein are methods for treating or preventing a cancer comprising administering an effective amount of a TOR kinase inhibitor and an effective amount of a cytidine analog to a patient having a cancer.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the cancer is not non-small cell lung cancer (NSCLC).

In one embodiment, the solid tumor is not non-small cell lung cancer (NSCLC).

In another embodiment, the solid tumor is glioblastoma multiforme (GBM).

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer (CRC).

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer, renal cancer, leiomyosarcoma, or paraganglioma.

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In other embodiments, the cancer is a hematologic tumor.

In other embodiments, the cancer is multiple myeloma.

In other embodiments, the cancer is non-Hodgkin lymphoma. In certain embodiments, the non-Hodgkin lymphoma is diffuse large B-cell lymphoma (DLBCL), follicular lymphoma (FL), acute myeloid leukemia (AML), mantle cell lymphoma (MCL), or ALK+ anaplastic large cell lymphoma. In one embodiment, the non-Hodgkin lymphoma is advanced solid non-Hodgkin lymphoma. In one embodiment, the non-Hodgkin lymphoma is diffuse large B-cell lymphoma (DLBCL).

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3δ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and hematologic tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In other embodiments, the cancer is myelodysplastic syndrome. In certain embodiments, the myelodysplastic syndrome subtype is refractory anemia (RA) or refractory anemia with ringed sideroblasts (if accompanied by neutropenia or thrombocytopenia or requiring transfusions), refractory anemia with excess blasts (RAEB), refractory anemia with excess blasts in transformation (RAEB-T), or chronic myelomonocytic leukemia (CMMoL).

In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with a cytidine analog to said patient. In certain embodiments, provided herein are methods for achieving a National Cancer Institute-Sponsored Working Group on Chronic Lymphocytic Leukemia (NCI-WG CLL) response definition of complete response, partial response or stable disease in a patient having leukemia, comprising administering an effective amount of a TOR kinase inhibitor in combination with a cytidine analog to said patient. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with a cytidine analog to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with a cytidine analog to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with a cytidine analog to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with a cytidine analog to said patient.

In certain embodiments, provided herein are methods for increasing survival without tumor progression of a patient having a cancer, comprising administering an effective amount of a TOR kinase inhibitor in combination with an effective amount of a cytidine analog to said patient.

In one embodiment, provided herein are methods for preventing or delaying a Response Evaluation Criteria in Solid Tumors (for example, RECIST 1.1) of progressive disease in a patient, comprising administering an effective amount of a TOR kinase inhibitor in combination with an effective amount of a cytidine analog to a patient having a cancer. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a patient compared to pre-treatment, comprising administering an effective amount of a TOR kinase inhibitor in combination with an effective amount of a cytidine analog to a patient having a cancer.

In certain embodiments, provided herein are methods for decreasing the size of a non-target lesion in a patient compared to pre-treatment, comprising administering an effective amount of a TOR kinase inhibitor in combination with an effective amount of a cytidine analog to a patient having a cancer.

In certain embodiments, provided herein are methods for achieving a reduction in the number of target lesions in a patient compared to pre-treatment, comprising administering an effective amount of a TOR kinase inhibitor in combination with an effective amount of a cytidine analog to a patient having a cancer.

In certain embodiments, provided herein are methods for achieving a reduction in the number of non-target lesions in a patient compared to pre-treatment, comprising administering an effective amount of a TOR kinase inhibitor in combination with an effective amount of a cytidine analog to a patient having a cancer.

In certain embodiments, provided herein are methods for achieving an absence of all target lesions in a patient, comprising administering an effective amount of a TOR kinase inhibitor in combination with an effective amount of a cytidine analog to a patient having a cancer.

In certain embodiments, provided herein are methods for achieving an absence of all non-target lesions in a patient, comprising administering an effective amount of a TOR kinase inhibitor in combination with an effective amount of a cytidine analog to a patient having a cancer.

In certain embodiments, provided herein are methods for treating a cancer, the methods comprising administering an effective amount of a TOR kinase inhibitor in combination with an effective amount of a cytidine analog to a patient having a cancer, wherein the treatment results in a complete response, partial response or stable disease, as determined by Response Evaluation Criteria in Solid Tumors (for example, RECIST 1.1).

In certain embodiments, provided herein are methods for treating a cancer, the methods comprising administering an effective amount of a TOR kinase inhibitor in combination with an effective amount of a cytidine analog to a patient having a cancer, wherein the treatment results in a reduction in target lesion size, a reduction in non-target lesion size and/or the absence of new target and/or non-target lesions, compared to pre-treatment.

In certain embodiments, provided herein are methods for treating a cancer, the methods comprising administering an effective amount of a TOR kinase inhibitor in combination with an effective amount of a cytidine analog to a patient having a cancer, wherein the treatment results in prevention or retarding of clinical progression, such as cancer-related cachexia or increased pain.

In some embodiments, provided herein are methods for treating a cancer, the methods comprising administering an effective amount of a TOR kinase inhibitor in combination with an effective amount of a cytidine analog to a patient having a cancer, wherein the treatment results in one or more of inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), and/or increased Overall Survival (OS), among others.

In some embodiments, the TOR kinase inhibitor is a compound as described herein. In one embodiment, the TOR kinase inhibitor is a compound of formula (I). In one embodiment, the TOR kinase inhibitor is a compound from Table A. In one embodiment, the TOR kinase inhibitor is Compound 1 (a TOR kinase inhibitor set forth herein having molecular formula $C_{21}H_{27}N_5O_3$). In one embodiment, the TOR kinase inhibitor is Compound 2 (a TOR kinase inhibitor set forth herein having molecular formula $C_{16}H_{16}N_8O$). In one embodiment, the TOR kinase inhibitor is Compound 3 (a TOR kinase inhibitor set forth herein having molecular formula $C_{21}H_{24}N_8O_2$). In one embodiment, the TOR kinase inhibitor is Compound 4 (a TOR kinase inhibitor set forth herein having molecular formula $C_{20}H_{25}N_5O_3$). In one embodiment, Compound 1 is 7-(6-(2-hydroxypropan-2-yl)pyridin-3-yl)-1-((1r,4r)-4-methoxycyclohexyl)-3,4-dihydropyrazino-[2,3-b]pyrazin-2(1H)-one, alternatively named 7-(6-(2-hydroxypropan-2-yl)pyridin-3-yl)-1-((trans)-4-methoxycyclohexyl)-3,4-dihydropyrazino[2,3-b]pyrazin-2(1H)-one, or 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one. In another embodiment, Compound 2 is 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one. In another embodiment, Compound 3 is 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one. In another embodiment, Compound 4 is 1-((trans)-4-hydroxycyclohexyl)-7-(6-(2-hydroxypropan-2-yl)pyridin-3-yl)-3,4-dihydropyrazino[2,3-b]pyrazin-2(1H)-one, alternatively named 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one. In one embodiment, Compound 4 is a metabolite of Compound 1.

A TOR kinase inhibitor administered in combination with a cytidine analog can be further combined with radiation therapy or surgery. In certain embodiments, a TOR kinase inhibitor is administered in combination with a cytidine analog to patient who is undergoing radiation therapy, has previously undergone radiation therapy or will be undergoing radiation therapy. In certain embodiments, a TOR kinase inhibitor is administered in combination with a cytidine analog to a patient who has undergone surgery, such as tumor removal surgery.

Further provided herein are methods for treating patients who have been previously treated for a cancer, as well as those who have not previously been treated. Further provided herein are methods for treating patients who have undergone surgery in an attempt to treat a cancer, as well as those who have not. Because patients with a cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

In certain embodiments, a TOR kinase inhibitor is administered in combination with a cytidine analog to a patient in cycles. Cycling therapy involves the administration of an active agent(s) for a period of time, followed by a rest for a period of time, and repeating this sequential administration. Cycling therapy can reduce the development of resistance, avoid or reduce the side effects, and/or improves the efficacy of the treatment.

In one embodiment, a TOR kinase inhibitor is administered in combination with a cytidine analog daily in single or divided doses for about 3 days, about 5 days, about one week, about two weeks, about three weeks, about four weeks (e.g., 28 days), about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, a TOR kinase inhibitor is administered in combination with a cytidine analog in single or divided doses for about 3 days, about 5 days, about one week, about two weeks, about three weeks, about four weeks (e.g., 28 days), about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, the methods provided herein comprise: i) administering to the subject a first daily dose of a TOR kinase inhibitor in combination with a cytidine analog; ii) optionally resting for a period of at least one day where a cytidine analog is not administered to the subject; iii) administering a second dose of a TOR kinase inhibitor in combination with a cytidine analog to the subject; and iv) repeating steps ii) to iii) a plurality of times.

In one embodiment, the methods provided herein comprise administering to the subject a dose of a cytidine analog on day 1, followed by administering a TOR kinase inhibitor in combination with a cytidine analog to the subject on day 2 and subsequent days.

In certain embodiments, a TOR kinase inhibitor in combination with a cytidine analog is administered continuously for between about 1 and about 52 weeks. In certain embodiments, a TOR kinase inhibitor in combination with a cytidine analog is administered continuously for about 0.5, 1, 2, 3, 4, 5, 6, 7, 8, 9, 10, 11, or 12 months. In certain embodiments, a TOR kinase inhibitor in combination with a cytidine analog is administered continuously for about 7, about 14, about 21, about 28, about 35, about 42, about 84, or about 112 days.

In certain embodiments, when a TOR kinase inhibitor is administered in combination with a cytidine analog, the TOR kinase inhibitor is administered continuously for 28 days, while a cytidine analog is administered continuously for 21 days followed by 7 days without administration of a cytidine analog. In one embodiment, in a 28 day cycle, a cytidine analog is administered alone on Day 1, a cytidine analog and the TOR kinase inhibitor are administered in combination on Days 2-21 and the TOR kinase inhibitor is administered alone on Days 22-28. In some such embodiments, starting with Cycle 2 both a cytidine analog and the TOR kinase inhibitor are administered on Day 1, a cytidine analog is continued through Day 21, while the TOR kinase inhibitor is continued through Day 28. The 28 day cycles, as described above, can be continued for as long needed, such as for 1, 2, 3, 4, 5, 6, 7, 8, 9, 10, 11 or 12 months or longer.

In certain embodiments, when a TOR kinase inhibitor is administered in combination with a cytidine analog, in a 28 day cycle, a cytidine analog is administered alone on Days 1-7 and the TOR kinase inhibitor is administered alone on Days 8-28. Such 28 day cycles can be continued for as long needed, such as for 1, 2, 3, 4, 5, 6, 7, 8, 9, 10, 11 or 12 months or longer.

In certain embodiments, when a TOR kinase inhibitor is administered in combination with a cytidine analog, in a 28 day cycle, a cytidine analog is administered in combination with a TOR kinase inhibitor on Days 1-7 and the TOR kinase inhibitor is administered alone on Days 8-28. Such 28 day cycles can be continued for as long needed, such as for 1, 2, 3, 4, 5, 6, 7, 8, 9, 10, 11 or 12 months or longer.

In certain embodiments, a cytidine analog is administered in combination with a TOR kinase inhibitor using a treatment cycle comprising administration of about 200 mg of the cytidine analog once per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog twice per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog once per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog twice per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog once per day for 21 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog twice per day for 21 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog three times per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 200 mg of the cytidine analog three times per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog once per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog twice per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog once per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog twice per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog once per day for 21 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog twice per day for 21 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog three times per day for 7 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, the formulation comprising the cytidine analog is administered using a treatment cycle comprising administration of about 300 mg of the cytidine analog three times per day for 14 or more days in combination with about 2.5 mg to about 50 mg (such as about 2.5 mg, about 10 mg, about 15 mg, about 16 mg, about 20 mg, about 30 mg or about 45 mg) once per day of a TOR kinase inhibitor. In certain embodiments, methods provided herein comprise administering a formulation comprising a cytidine analog in combination with a TOR kinase inhibitor using one or more of the cycles provided herein, and repeating one or more of the cycles for a period of, e.g., about 1, 2, 3, 4, 5, 6, 7, 8, 9, 10, 11, 12, or greater than 12 months. A TOR kinase inhibitor and a cytidine analog can each be independently administered once (QD), twice (BD) or three times (TID) per day.

In certain embodiments, when a TOR kinase inhibitor is administered in combination with a cytidine analog, the TOR kinase inhibitor is administered at an amount of about 2.5 mg to about 50 mg per day (such as about 2.5 mg, about 10 mg, about 15 mg, about 20 mg, about 30 mg or about 45 mg per day) and a cytidine analog is administered at an amount of about 50 mg/m$^2$/day to about 2,000 mg/m$^2$/day (such as about 50 mg/m$^2$/day, about 75 mg/m$^2$/day, about 100 mg/m$^2$/day, about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day). In certain embodiments, about 2.5 mg per day of a TOR kinase inhibitor is administered in combination with about 75 mg/m$^2$/day or about 100 mg/m$^2$/day of a cytidine analog. In certain embodiments, about 10 mg per day of a TOR kinase inhibitor is administered in combination with about 75 mg/m$^2$/day or about 100 mg/m$^2$/day of a cytidine analog. In certain embodiments, about 15 mg per day of a TOR kinase inhibitor is administered in combination with about 75 mg/m$^2$/day or about 100 mg/m$^2$/day of a cytidine analog. In certain embodiments, about 20 mg per day of a TOR kinase inhibitor is administered in combination with about 75 mg/m$^2$/day or about 100 mg/m$^2$/day of a cytidine analog. In certain embodiments, about 30 mg per day of a TOR kinase inhibitor is administered in combination with about 75 mg/m$^2$/day or about 100 mg/m$^2$/day of a cytidine analog. In certain embodiments, about 45 mg per day of a TOR kinase inhibitor is administered in combination with about 75 mg/m$^2$/day or about 100 mg/m$^2$/day of a cytidine analog.

In certain embodiments, when a TOR kinase inhibitor is administered in combination with a cytidine analog, the TOR kinase inhibitor is administered at an amount of about 2.5 mg to about 50 mg per day (such as about 2.5 mg, about 10 mg, about 15 mg, about 16 mg, about 20 mg, about 30 mg or about 45 mg per day) and a cytidine analog is administered at an amount of about 50 mg to about 1000 mg per day (such as about 50 mg, about 60 mg, about 70 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 260 mg, about 280 mg, about 300 mg, about 320 mg, about 340 mg, about 350 mg, about 360 mg, about 380 mg, about 400 mg, about 420 mg, about 450 mg, about 480 mg, about 500 mg, about 600 mg, about 700 mg, about 800 mg, about 900 mg, or about 1,000 mg per day). In certain embodiments, about 2.5 mg per day of a TOR kinase inhibitor is administered in combination with about 200 mg or about 300 mg per day of a cytidine analog. In certain embodiments, about 10 mg per day of a TOR kinase inhibitor is administered in combination with about 200 mg or about 300 mg per day of a cytidine analog. In certain embodiments, about 15 mg per day of a TOR kinase inhibitor is administered in combination with about 200 mg or about 300 mg per day of a cytidine analog. In certain embodiments, about 16 mg per day of a TOR kinase inhibitor is administered in combination with about 200 mg or about 300 mg per day of a cytidine analog. In certain embodiments, about 20 mg per day of a TOR kinase inhibitor is administered in combination with about 200 mg or about 300 mg per day of a cytidine analog. In certain embodiments, about 30 mg per day of a TOR kinase inhibitor is administered in combination with about 200 mg or about 300 mg per day of a cytidine analog. In certain embodiments, about 45 mg per day of a TOR kinase inhibitor is administered in combination with about 200 mg or about 300 mg per day of a cytidine analog.

In certain embodiments, when a TOR kinase inhibitor is administered in combination with a cytidine analog, the TOR kinase inhibitor:cytidine analog ratio is from about 1:1 to about 1:30. In certain embodiments, when a TOR kinase inhibitor is administered in combination with a cytidine analog, the TOR kinase inhibitor:cytidine analog ratio is less than about 1:1, less than about 1:10 or less than about 1:30. In certain embodiments, when a TOR kinase inhibitor is administered in combination with a cytidine analog, the TOR kinase inhibitor:cytidine analog ratio is about 1:1, about 1:10 or about 1:30.

In certain embodiments, when a TOR kinase inhibitor is administered in combination with a cytidine analog, the amount of a cytidine analog administered may range, e.g., between about 50 mg/m$^2$/day and about 2,000 mg/m$^2$/day, between about 100 mg/m$^2$/day and about 1,000 mg/m$^2$/day, between about 50 mg/m$^2$/day and about 200 mg/m$^2$/day, between about 50 mg/m$^2$/day and about 100 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 50 mg/m$^2$/day, about 75 mg/m$^2$/day, about 100 mg/m$^2$/day, about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day. In certain embodiments, particular dosages are, e.g., up to about 100 mg/m$^2$/day, up to about 120 mg/m$^2$/day, up to about 140 mg/m$^2$/day, up to about 150 mg/m$^2$/day, up to about 180 mg/m$^2$/day, up to about 200 mg/m$^2$/day, up to about 220 mg/m$^2$/day, up to about 240 mg/m$^2$/day, up to about 250 mg/m$^2$/day, up to about 260 mg/m$^2$/day, up to about 280 mg/m$^2$/day, up to about 300 mg/m$^2$/day, up to about 320 mg/m$^2$/day, up to about 350 mg/m$^2$/day, up to about 380 mg/m$^2$/day, up to about 400 mg/m$^2$/day, up to about 450 mg/m$^2$/day, up to about 500 mg/m$^2$/day, up to about 750 mg/m$^2$/day, or up to about 1000 mg/m$^2$/day.

In certain embodiments, when a TOR kinase inhibitor is administered in combination with a cytidine analog, the amount of a cytidine analog administered may range, e.g., between about 5 mg/day and about 2,000 mg/day, between about 10 mg/day and about 2,000 mg/day, between about 20 mg/day and about 2,000 mg/day, between about 50 mg/day and about 1,000 mg/day, between about 100 mg/day and about 600 mg/day, between about 100 mg/day and about 500 mg/day, between about 150 mg/day and about 500 mg/day, between about 250 mg/day and about 350 mg/day, or between about 150 mg/day and about 250 mg/day. In certain embodiments, particular dosages are, e.g., about 10 mg/day, about 20 mg/day, about 50 mg/day, about 75 mg/day, about 100 mg/day, about 120 mg/day, about 150 mg/day, about 180 mg/day, about 200 mg/day, about 240 mg/day, about 250 mg/day, about 280 mg/day, about 300 mg/day, about 320 mg/day, about 350 mg/day, about 360 mg/day, about 400 mg/day, about 450 mg/day, about 500 mg/day, about 600 mg/day, about 700 mg/day, about 800 mg/day, about 900 mg/day, about 1,000 mg/day, about 1,200 mg/day, or about 1,500 mg/day. In certain embodiments, particular dosages are, e.g., up to about 10 mg/day, up to about 20 mg/day, up to about 50 mg/day, up to about 75 mg/day, up to about 100 mg/day, up to about 120 mg/day, up to about 150 mg/day, up to about 200 mg/day, up to about 250 mg/day, up to about 300 mg/day, up to about 350 mg/day, up to about 400 mg/day, up to about 450 mg/day, up to about 500 mg/day, up to about 600 mg/day, up to about 700 mg/day, up to about 800 mg/day, up to about 900 mg/day, up to about 1,000 mg/day, up to about 1,200 mg/day, or up to about 1,500 mg/day.

5.6 Pharmaceutical Compositions and Routes of Administration

Provided herein are compositions comprising an effective amount of a TOR kinase inhibitor and an effective amount of a cytidine analog and compositions, comprising an effective amount of a TOR kinase inhibitor and a cytidine analog and a pharmaceutically acceptable carrier or vehicle.

In some embodiments, the pharmaceutical compositions described herein are suitable for oral, parenteral, mucosal, transdermal or topical administration.

The compositions can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the TOR kinase inhibitor in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a TOR kinase inhibitor and the dose of a cytidine analog to be administered to a patient is rather widely variable and can be subject to the judgment of a health-care practitioner. In general, the TOR kinase inhibitors and a cytidine analog can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the TOR kinase inhibitor administered will depend on such factors as the solubility of the active component, the formulation used and the route of administration.

In another embodiment, provided herein are unit dosage formulations that comprise between about 1 mg and about 2000 mg, about 1 mg and about 200 mg, about 35 mg and about 1400 mg, about 125 mg and about 1000 mg, about 250 mg and about 1000 mg, about 500 mg and about 1000 mg, about 1 mg to about 30 mg, about 1 mg to about 25 mg or about 2.5 mg to about 20 mg of a TOR kinase inhibitor alone or in combination with a cytidine analog. In another embodiment, provided herein are unit dosage formulations that comprise 1 mg, 2.5 mg, 5 mg, about 7.5 mg, 8 mg, 10 mg, 15 mg, 20 mg, 30 mg, 35 mg, 45 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a TOR kinase inhibitor alone or in combination with a cytidine analog. In another embodiment, provided herein are unit dosage formulations that comprise about 2.5 mg, about 10 mg, about 15 mg, about 20 mg, about 30 mg or about 45 mg of a TOR kinase inhibitor alone or in combination with a cytidine analog. In a particular embodiment, provided herein are unit dosage formulations that comprise about 5 mg, about 7.5 mg and about 10 mg of a TOR kinase inhibitor alone or in combination with a cytidine analog.

In a particular embodiment, provided herein are unit dosage formulations comprising about 7.5 mg, about 8 mg, about 10 mg, about 15 mg, about 30 mg, about 45 mg, about 50 mg, about 75 mg, about 100 mg or about 400 mg of a TOR kinase inhibitor in combination with a cytidine analog.

In another embodiment, provided herein are unit dosage formulations that comprise between about 5 mg and about 2,000 mg, between about 10 mg and about 2,000 mg, between about 20 mg and about 2,000 mg, between about 50 mg and about 1,000 mg, between about 100 mg and about 600 mg, between about 100 mg and about 500 mg, between about 150 mg and about 500 mg, between about 250 mg and about 350 mg, or between about 150 mg and about 250 mg of a cytidine analog alone or in combination with a TOR kinase inhibitor. In certain embodiments, particular amounts of a cytidine analog are, e.g., about 10 mg, about 20 mg, about 50 mg, about 75 mg, about 100 mg, about 120 mg, about 150 mg, about 180 mg, about 200 mg, about 240 mg, about 250 mg, about 300 mg, about 320 mg, about 350 mg, about 360 mg, about 400 mg, about 420 mg, about 450 mg, about 480 mg, about 500 mg, about 600 mg, about 700 mg, about 800 mg, about 900 mg, about 1,000 mg, about 1,200 mg, or about 1,500 mg. In certain embodiments, particular amounts of a cytidine analog are, e.g., up to about 10 mg, up to about 20 mg, up to about 50 mg, up to about 75 mg, up to about 100 mg, up to about 120 mg, up to about 150 mg, up to about 200 mg, up to about 250 mg, up to about 300 mg, up to about 350 mg, up to about 400 mg, up to about 450 mg, up to about 500 mg, up to about 600 mg, up to about 700 mg, up to about 800 mg, up to about 900 mg, up to about 1,000 mg, up to about 1,200 mg, or up to about 1,500 mg.

In certain embodiments, provided herein are unit dosage formulations wherein the TOR kinase inhibitor:cytidine analog ratio is from about 1:1 to about 1:10. In certain embodiments, provided herein are unit dosage formulations wherein the TOR kinase inhibitor:cytidine analog ratio is less than about 1:1, less than about 1:3 or less than about 1:10. In certain embodiments, provided herein are unit dosage formulations wherein the TOR kinase inhibitor:cytidine analog ratio is about 1:1, about 1:3 or about 1:10.

A TOR kinase inhibitor can be administered in combination with a cytidine analog once, twice, three, four or more times daily.

A TOR kinase inhibitor can be administered in combination with a cytidine analog orally for reasons of convenience. In one embodiment, when administered orally, a TOR kinase inhibitor in combination with a cytidine analog is administered with a meal and water. In another embodiment, the TOR kinase inhibitor in combination with a cytidine analog is dispersed in water or juice (e.g., apple juice or orange juice) and administered orally as a suspension. In another embodiment, when administered orally, a TOR kinase inhibitor in combination with a cytidine analog is administered in a fasted state.

The TOR kinase inhibitor can also be administered in combination with a cytidine analog intravenously, such as intravenous infusion, or subcutaneously, such as subcutaneous injection. The mode of administration is left to the discretion of the health-care practitioner, and can depend in-part upon the site of the medical condition.

In one embodiment, provided herein are capsules containing a TOR kinase inhibitor in combination with a cytidine analog without an additional carrier, excipient or vehicle.

In another embodiment, provided herein are compositions comprising an effective amount of a TOR kinase inhibitor, an effective amount of a cytidine analog, and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a TOR kinase inhibitor with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders. Illustrative tablet formulations comprising Compound 1 are provided herein.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a TOR kinase inhibitor in combination with a cytidine analog as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the TOR kinase inhibitor in combination with a cytidine analog can be delayed or prolonged by proper formulation. For example, a slowly soluble pellet of the TOR kinase inhibitor in combination with a cytidine analog can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the TOR kinase inhibitor in combination with a cytidine analog in oily or emulsified vehicles that allow it to disperse slowly in the serum.

In certain embodiments, Compound 1 is administered in a formulation set forth in U.S. Patent Application Publication No. 2013-0142873, published Jun. 6, 2013, which is incorporated herein in its entirety (see particularly paragraph [0323] to paragraph [0424], and paragraph [0636] to paragraph [0655]). In other embodiments, Compound 1 is administered in a formulation set forth in U.S. Provisional Patent Application No. 61/828,506, filed May 29, 2013, which is incorporated herein in its entirety (see particularly paragraph [0246] to paragraph [0403], and paragraph [0571] to paragraph [0586]).

In certain embodiments, Compound 2 is administered in a formulation set forth in U.S. Provisional Application No. 61/813,064, filed Apr. 17, 2013, which is incorporated herein in its entirety (see particularly paragraph [0168] to paragraph [0189] and paragraph [0262] to paragraph [0294]). In other embodiments, Compound 2 is administered in a formulation set forth in U.S. Provisional Patent Application No. 61/911,201, filed Dec. 3, 2013, which is incorporated herein in its entirety (see particularly paragraph [0170] to paragraph [0190], and paragraph [0264] to paragraph [0296]).

5.7 Kits

In certain embodiments, provided herein are kits comprising a TOR kinase inhibitor and a cytidine analog.

In certain embodiments, provided herein are kits comprising one or more unit dosage forms of a TOR kinase inhibitor, such as those described herein, and one or more unit dosage forms of a cytidine analog, such as those described herein.

In certain embodiments, the kits provided herein further comprise instructions for use, such as for administering a TOR kinase inhibitor and a cytidine analog.

6. EXAMPLES 6.1 Biochemical Assays mTOR HTR-FRET Assay.

The following is an example of an assay that can be used to determine the TOR kinase inhibitory activity of a test compound. TOR kinase inhibitors were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PV4753) was diluted in this buffer to an assay concentration of 0.200 μg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple TOR buffer is added 0.5 μL of test compound in DMSO. To initiate the reaction 5 μL of ATP/Substrate solution was added to 20 μL of the Simple TOR buffer solution (control) and to the compound solution prepared above. The assay was stopped after 60 min by adding 5 μL of a 60 mM EDTA solution; 10 μL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

TOR kinase inhibitors were tested in the mTOR HTR-FRET assay and were found to have activity therein, with certain compounds having an $IC_{50}$ below 10 μM in the assay, with some compounds having an $IC_{50}$ between and 0.005 nM and 250 nM, others having an $IC_{50}$ between and 250 nM and 500 nM, others having an $IC_{50}$ between 500 nM and 1 μM, and others having an $IC_{50}$ between 1 μM and 10 μM.

DNA-PK Assay.

DNA-PK assay is performed using the procedures supplied in the Promega DNA-PK assay kit (catalog # V7870). DNA-PK enzyme can be purchased from Promega (Promega cat#V5811).

Selected TOR kinase inhibitors as described herein have, or are expected to have, an $IC_{50}$ below 10 μM in this assay, with some TOR kinase inhibitors as described herein having an $IC_{50}$ below 1 μM, and others having an $IC_{50}$ below 0.10 μM.

6.2 Cell Based Assays

Materials and Methods.

Cell lines and cell culture: Cell lines were purchased from American Type Culture Collection (ATCC) and maintained in culture medium recommended by ATCC. Ovarian cancer cell lines that were used or can be used include the following: Ovcar-3, Ovcar-4, Ovcar-5, Oncar-8 and Caov-3. Multiple myeloma (MM) cell lines that were used or can be used include the following: NCI-H929, LP-1, MM1.s, U266B1, DF-15 and RPMI-8226 human MM-derived cell lines. The REVLIMID® resistant cell lines H929/R1 and H929/R4 were established by continuous exposure of H929 parental cells (H929) to increasing concentrations of REVLIMID® for a minimum of 5 months. The control cell line H929/D was established by continuous exposure of H929 parental cells to 0.1% DMSO. The established H929/R1 and H929/R4 were pulsed once every 3 days with 10 μM REVLIMID, whereas H929/D was pulsed once every 3 days with 0.1% DMSO. Hepatocellular cancer, breast cancer, lung cancer and melanoma cell lines were purchased from commercial sources (ATCC, DSMZ, HSRRB) and routinely maintained in RPMI1640 or DMEM containing 10% fetal bovine serum at 37° C. with 5% $CO_2$. Hepatocellular carcinoma (HCC) cell lines that were used or can be used include the following: Hep3B, HepG2, HuH-7, PLC-PRF-5, SK-HEP-1, SNU-182, SNU-387, SNU-398, SNU-423, SNU-449, and SNU-387.

Cell Viability Assay Ovarian Cell Lines.

Cell viability was assessed using the Cell Titer-Glo® Luminescent Cell Viability Assay, Catalog Number G7570 (Promega Corporation, Madison, Wis.). The assay is a homogenous method of determining the number of viable cells in culture based on quantitation of the adenosine triphosphate (ATP) present, an indicator of metabolically active cells. The homogenous assay procedure involves adding the single reagent (CellTiter-Glo Reagent) directly to cells cultured in serum-supplemented medium. Cells were plated into a 96-well flat bottom plate (Costar Catalog Number 33595) at densities that were previously optimized for each cell line. The cells were incubated overnight in 5% $CO_2$ at 37° C. The following day, compound dilutions were prepared and all concentrations were assayed in triplicate. The cells were incubated with a TOR kinase inhibitor or a TOR kinase inhibitor and a second active agent, in 5% $CO_2$ at 37° C. for 3 days. After a 3-day incubation period, 100 μL, of CellTiter-Glo reagent was added to each well for 2 min with shaking and further incubated for 10 min (no shaking) at room temperature to stabilize the signal. The luminescence was measured on the VICTOR X2 multilabel plate reader. The percent growth inhibition was calculated using the DMSO control in the same plate (no compound) response as 100% cell growth. For single compound treatments (TORKi and second active agents separately), the average values from triplicates were plotted to obtain $IC_{50}$ values using software XLfit from IDBS. The formula used for determining $IC_{50}$ in XLfit was model number 205, which utilizes a 4 Parameter Logistic Model or Sigmoidal Dose-Response Model to calculate the $IC_{50}$ values. Results are set forth in Table 1.

Measurement of Synergism of Cell Proliferation Inhibition Using a TOR Kinase Inhibitor in Combination with a Second Active Agent.

The cell viability assay was first performed with the TOR kinase inhibitor and the individual second active agents, to determine the dose range for subsequent combination studies. To maintain similar potency for the TOR kinase inhibitor and the second active agent, the highest combination dose started at the approximate $IC_{50}$ for each compound, with a constant ratio of 1:1 or 1:10 during dilutions. The TOR kinase inhibitor and the second active agent were each added to one well containing a final concentration of 0.2% DMSO (in triplicate). In the same plate in triplicate, the cells were treated with the TOR kinase inhibitor and each second active agent either simultaneously or sequentially (containing 0.2% DMSO). The number of cells affected by compound treatment was normalized to the DMSO control (100% viability) and the data was imported into the CalcuSyn software (V2.1, Biosoft). Synergism was quantitated by the combination index (CI) using CalcuSyn according to Chou-Talalay's CI method with mathematical modeling and simulations. The CI value indicates strong synergism if the value is between 0.1-0.3, synergism between 0.3-0.7, moderate synergism 0.7-0.85, slight synergism 0.85-0.90 and nearly additive 0.90-1.10 (*Trends Pharmacol. Sci.* 4, 450-454, 1983). $ED_{50}$ is the median effect dose at which a 50% growth inhibition is achieved. Results are set forth in Table 1.

TABLE 1

Combination index (CI) at the $ED_{50}$ in ovarian cancer cell lines for Compound 1, Compound 3 and VIDAZA ®.

| Cell line | CI at ED50 | |
|---|---|---|
| | Compound 3 | Compound 1 |
| Ovcar-3 | 0.55 | 1.23 |
| Ovcar-4 | 0.61 | 0.99 |
| Ovcar-5 | 0.76 | 0.92 |
| Ovcar-8 | 0.81 | 0.99 |
| Caov-3 | 0.92 | 1.08 |

Cell Viability Assay for Hepatocellular Cell Lines.

The TOR kinase inhibitor and second agent were added to an empty 384-well flat, clear bottom, black polystyrene, TC-Treated plate (Cat#3712, Corning, Mass.) via an acoustic dispenser (EDC Biosystems). The TOR kinase inhibitor was serially diluted 3-fold across the plate for nine concentrations and the second agent was serially diluted 3-fold down the plate for seven concentrations. An orthogonal titration of the two agents was performed to create 63 different combinations of the compounds. Both compounds were also added alone to determine their affects as single agents. DMSO (no compound) was used as control for 100% viability and background (no cells). Final assay DMSO concentration was 0.2% (v/v). Cells were added directly on top of the compounds at an optimized density to ensure that the cell growth was within the linear detection range of the assay after four days in culture. At its endpoint, cell viability was determined using Promega's CellTiter-Glo Luminescent Cell Viability Assay (Cat# G7573, Promega, Wis.) using the manufacturer's standard operating procedures. Background subtracted luminescence counts were converted to percentages of cell viability with respect to DMSO treated control cells. Dose response curves were generated using XLFit4 (IDBS, UK) by fitting the percentage of control data at each concentration using a 4 Parameter Logistic Model/Sigmoidal Dose-Response Model [y=(A+((B−A)/(1+((C/x)^D))))]. To evaluate the combinatory effect of the two agents on a cell line, data was analyzed by comparing its combinatory response against the theoretical additive response of the two agents alone. The expected additive effect of two agents (A and B) was calculated using the fractional product method (Webb 1961): (fu)A,B=(fu)A×(fu)B where fu=fraction unaffected by treatment. Synergism of a combination is determined when the observed fraction unaffected in combination is less than (fu)A,B, while an additive effect is determined when the observed fraction unaffected in combination=(fu)A,B. Results are set forth in Table 2.

TABLE 2

Combination of a TOR kinase inhibitor and second active agents in selected HCC cell lines With Vidaza

| HCC cell line | Combination | Synergism |
|---|---|---|
| Hep3B | Compound 1 + VIDAZA ® | Weak Synergy |
| HepG2 | Compound 1 + VIDAZA ® | Weak Synergy |
| PLC-PRF-5 | Compound 1 + VIDAZA ® | Additive |
| SK-HEP-1 | Compound 1 + VIDAZA ® | Synergy |
| SNU-387 | Compound 1 + VIDAZA ® | Additive |
| SNU-398 | Compound 1 + VIDAZA ® | Additive |
| SNU-423 | Compound 1 + VIDAZA ® | Additive |
| SNU-449 | Compound 1 + VIDAZA ® | Additive |
| SNU-475 | Compound 1 + VIDAZA ® | Additive |

Compound 1 Combinatorial Effects with 5-AZA in the Human Hepatocellular Carcinoma Anchorage Independent Growth Assay.

Summary.

The effect of Compound 1 on anchorage-independent growth (AIG) was assessed by colony formation assay in 2 Human Hepatocellular Carcinoma ("HHC") cell lines, HepG2 and SK-Hep-1. Compound 1 showed dose-dependent and significant anti-colony forming activity at concentrations of 0.1 to 100 µM in both cell lines. Compound 1 synergistically inhibited colony formation in both cell lines with 5-AZA.

Study Objectives.

The objective of this study was to evaluate the direct effects of Compound 1 and combinations of Compound 1 with 5-AZA on tumor cell anchorage-independent growth in 2 HHC tumor cell lines. This evaluation was performed in colony formation assays.

Materials and Methods.

Study Materials.

Cell Lines/Cells. Human cell lines HepG2 and SK-Hep-1 cells were obtained from American Type Culture Collection (ATCC; Manassas, Va.). Cells were cultured in DMEM (Dulbecco's Modified Eagle's Medium) (Mediatech; Mannasas, Va.) with 10% Premium FBS (Lonza, Walkersville, Md.).

Experimental Procedures.

(1) Single Agent Colony Formation Assay. Nobel Agar (1.2 grams; BD; Franklin Lakes, N.J.) was placed in a 100-mL sterile bottle. Sterile water (100 mL) was added and microwaved until the agar boiled. Equal volumes of agar and 2×RPMI medium (ECE Scientific; Doylestown, Pa.) were mixed and 300 µL were transferred to each well in a 24-well flat bottom plate (BD; Franklin Lakes, N.J.). Plates were kept at 4° C. until the agar solidified. Cultures of HepG2 and SK-Hep-1 cells were harvested and resuspended in culture medium at $3.6\times10^3$ cells/mL. Equal volumes of agar, 2×RPMI, and cell suspension (1:1:1) were mixed in a sterile tube and 500 μL/well were immediately transferred into the 24-well plates. Plates were kept at 4° C. until the agar solidified. Culture medium (500 μL) containing compound or DMSO was added to each well (final DMSO concentration for each treatment was 0.2%). Compound 1 was tested at final concentrations of 0.1, 0.3, 1, 3, 10 and 30 μM. 5-AZA was tested at final concentrations of 1, 3 and 10 μM. Cell treatments were set up in triplicate. Cells were incubated for 8-10 days at 37° C. in a 5% $CO_2$ atmosphere. Photographs (2× magnification) of each well were taken using a Nikon DXM1200 Digital Camera and Nikon ACT1 software and saved as a TIFF file. ImageQuant TL (GE Healthcare; Piscataway, N.J.) Colony Count Software was used to count colonies. (2) Combination Study Colony Formation Assay. Nobel Agar (1.2 grams; BD; Franklin Lakes, N.J.) was placed in a 100-mL sterile bottle. Sterile water (100 mL) was added and microwaved until the agar boiled. Equal volumes of agar and 2×RPMI medium (ECE Scientific; Doylestown, Pa.) were mixed and 300 μL were transferred to each well in a 24-well flat bottom plate (BD; Franklin Lakes, N.J.). Plates were kept at 4° C. until the agar solidified. Cultures of HepG2 and SK-Hep-1 cells were harvested and resuspended in culture medium at $3.6\times10^3$ cells/mL. Equal volumes of agar, 2×RPMI, and cell suspension (1:1:1) were mixed in a sterile tube and 500 μL/well were immediately transferred into the 24-well plates. Plates were kept at 4° C. until the agar solidified. Culture medium (500 μL) containing compound or DMSO was added to each well (final DMSO concentration for each treatment was 0.2%). Cells were treated with single treatment as follows: Compound 1 was tested at final concentrations of 0.1 and 0.3 μM. 5-AZA was tested at 3 μM. Combinations of Compound 1 at 0.1 and 0.3 μM were tested with 3 μM 5-AZA. Cell treatments were set up in triplicate. Cells were incubated for 8-10 days at 37° C. in a 5% $CO_2$ atmosphere. Photographs (2× magnification) of each well were taken using a Nikon DXM1200 Digital Camera and Nikon ACT1 software and saved as a TIFF file. ImageQuant TL (GE Healthcare; Piscataway, N.J.) Colony Count Software was used to count colonies.

Data Analysis.

The percentage inhibition of colony formation was calculated by normalizing to DMSO controls (100% control). Significance versus the DMSO control was calculated using One Way ANOVA and Dunnett's Post test or unpaired t tests using GraphPad Prism v5.01. To evaluate the combinatory effect, data from the three independent experiments were analyzed by comparing the combinatory response against the theoretical additive response of the two agents.

The expected additive effect of two agents (A and B) was calculated using the fractional product method [Webb]: $(fu)A,B=(fu)A\times(fu)B$; where fu=fraction unaffected by treatment. A synergism of a combination is determined when the observed fraction unaffected in combination is significantly less than (fu)A,B, whereas an additive effect is determined when the observed fraction unaffected in combination equals (fu)A,B. A partially additive effect occurs when the observed fraction unaffected is significantly greater than (fu)A,B.

Results.

Results from colony formation assays with single agent treatments in HepG2 cells are presented in FIG. 1. HepG2 cells treated with 0.1, 0.3, 1, 3, 10, and 30 μM Compound 1 showed significant inhibition of colony formation at 74, 57, 33, 24, 16 and 11% of control, respectively (p value<0.001). 5-AZA significantly inhibited 43-76% of control of colony formation at 1, 3 and 10 μM as showed in FIG. 2 (p value<0.001).

Results from colony formation assays with single agent treatments in SK-Hep-1 cells are presented in FIG. 3. Significant inhibition of colony formation (0-45% of control) was observed in SK-Hep-1 cells after treatment with 0.3-30 μM Compound 1 (p value<0.001). Treatments with 3 μM Compound 1 and higher resulted in 100% inhibition of colony formation. 5-AZA significantly inhibited 38% of control of colony formation at 10 μM as showed in FIG. 4 (p value<0.001).

Results from the Compound 1 combination colony formation assays in HepG2 cells are presented in FIG. 5 and Table 3. FIG. 5 shows that the 0.1 μM Compound 1 plus 3 μM 5-AZA had a non-significant additive effect on colony formation while 0.3 μM Compound 1 in combination with 3 μM 5-AZA synergistically reduced the number of HepG2 colonies (p value<0.001).

Results from the Compound 1 combination colony formation assays in SK-Hep-1 cells are presented in FIG. 6 and Table 4. FIG. 6 shows that the combination of Compound 1 plus 3 μM 5-AZA synergistically reduced the number of SK-Hep-1 colonies (p value<0.05).

Conclusions.

The effect of Compound 1 in combination with 5-AZA, on anchorage-independent growth was assessed by colony formation assay in HepG2 and SK-Hep-1 cells. Compound 1 exhibited dose-dependent and significant anti-colony forming in both cell lines at concentrations of 0.1 to 100 μM.

In HepG2 cells, Compound 1 in combination with 5-AZA had additive to synergistic effects.

In SK-HEP-1 cells, Compound 1 in combination with 5-AZA had synergistic effects.

TABLE 3

Results of the Compound 1 HepG2 Colony Formation Assay

| Compound | Colony Formation (% of Control) | Combination Effect | p value of Actual vs Theoretical % Control |
|---|---|---|---|
| 0.1 μM Compound 1 + 3 μM 5-AZA | 45 | additive | ns |
| 0.3 μM Compound 1 + 3 μM 5-AZA | 83 | synergism | *** |

HepG2 cells were plated in agar and incubated with compound for 8 days before colonies were counted. Data were calculated as the percentage of inhibition relative to the cells treated with DMSO only=0% inhibition. Results represents the mean of n=3 experiments in triplicate. Fractional product method was used to calculate combination effects of compound combinations. ***p<0.001. ns=not significant.

TABLE 4

Results of the Compound 1 SK-Hep-1 Colony Formation Assay

| Compound | Colony Formation (% of Control) | Combination Effect | p value of Actual vs Theoretical % Control |
|---|---|---|---|
| 0.1 μM Compound 1 + 3 μM 5-AZA | 35 | synergism | * |

TABLE 4-continued

Results of the Compound 1 SK-Hep-1 Colony Formation Assay

| Compound | Colony Formation (% of Control) | Combination Effect | p value of Actual vs Theoretical % Control |
|---|---|---|---|
| 0.3 µM Compound 1 + 3 µM 5-AZA | 45 | synergism | * |

SK-Hep-1 cells were plated in agar and incubated with compound for 8 days before colonies were counted. Data were calculated as the percentage of inhibition relative to the cells treated with DMSO only=0% inhibition. Results represents the mean of n=3 experiments in triplicate. Fractional product method was used to calculate combination effects of compound combinations. *p<0.05 vs theoretical additivity by unpaired t test.

Compound 2 Combinatorial Effects with 5-AZA in Breast Cancer Cell Lines.

Anti-Proliferation Assay.

Cells were thawed from a liquid nitrogen preserved state. Once cells expanded and divided at their expected doubling times, screening began. Cells were seeded in growth media in 384-well tissue culture treated plates at cell densities as listed in Table 5.

TABLE 5

Breast cancer cell line panel

| Cell Line Name | Tumor | Growth Media | Cell Density (cells/well) |
|---|---|---|---|
| BT-20 | Carcinoma | Eagles MEM with 10% FBS | 500 |
| BT-474 | Carcinoma | Hybri-Care with 10% FBS | 500 |
| BT-549 | Carcinoma, Ductal | RPMI with 10% FBS and 0.023 IU/ml Bovine Insulin | 500 |
| HCC1187 | Carcinoma, Ductal | RPMI with 10% FBS | 500 |
| HCC-1428 | Adenocarcinoma | RPMI with 10% FBS | 500 |
| HCC1806 | Carcinoma, Ductal | RPMI with 10% FBS | 500 |
| HCC1937 | Carcinoma, Ductal | RPMI with 10% FBS | 500 |
| HCC70 | Carcinoma, Ductal | RPMI with 10% FBS | 500 |
| Hs-578-T | Carcinoma | DMEM with 10% FBS and 0.01 mg/ml Bovine Insulin | 500 |
| MCF7 | Adenocarcinoma | Eagles MEM with 10% FBS and 0.01 mg/ml Bovine Insulin | 500 |
| MDA-MB-157 | Carcinoma | RPMI with 10% FBS (with 5% $CO_2$) | 500 |
| MDA-MB-231 | Adenocarcinoma | RPMI with 10% FBS (with 5% $CO_2$) | 500 |
| MDA-MB-436 | Adenocarcinoma | RPMI with 10% FBS (with 5% $CO_2$) plus Supplements | 500 |
| MDA-MB-453 | Adenocarcinoma | RPMI with 10% FBS (with 5% $CO_2$) | 500 |
| MDA-MB-468 | Adenocarcinoma | DMEM with 10% FBS (with 5% $CO_2$) | 500 |
| HCC1500 | Carcinoma, Ductal | RPMI with 10% FBS | 500 |
| MDA-MB-175-VII | Carcinoma, Ductal | RPMI with 10% FBS | 500 |

Cells were equilibrated in assay plates via centrifugation and placed in incubators attached to the Dosing Modules at 37° C. for twenty-four hours before treatment. At the time of treatment, a set of assay plates (which did not receive treatment) were collected and ATP levels were measured by adding ATP Lite (Perkin Elmer). These T zero ($T_0$) plates were read using ultra-sensitive luminescence on Envision Plate Readers. Treated assay plates were incubated with compound (single compound or combination) for seventy-two hours. After seventy-two hours, plates were developed for endpoint analysis using ATPLite. All data points were collected via automated processes; quality controlled; and analyzed. Assay plates were accepted if they passed the following quality control standards: relative luciferase values were consistent throughout the entire experiment, Z-factor scores were greater than 0.6, untreated/vehicle controls behaved consistently on the plate. The calculation for synergy score is provided below.

Growth Inhibition (GI) was used as a measure of cell viability. The cell viability of vehicle was measured at the time of dosing ($T_0$) and after seventy-two hours ($T_{72}$). A GI reading of 0% represents no growth inhibition—cells treated with compound and $T_{72}$ vehicle signals are matched. A GI 100% represents complete growth inhibition—cells treated by compound and $T_0$ vehicle signals are matched. Cell numbers have not increased during the treatment period in wells with GI 100% and may suggest a cytostatic effect for compounds reaching a plateau at this effect level. A GI 200% represents complete death of all cells in the culture well. Compounds reaching an activity plateau of GI 200% are considered cytotoxic. GI was calculated by applying the following test and equation:

If $T<V_0$: $100*[1-(T-V_0)/V_0]$

If $T \geq V_0$: $100*[1-(T-V_0)/(V-V_0)]$

Where T is the signal measure for a test article, V is the vehicle-treated control measure, and $V_0$ is the vehicle control measure at time zero. This formula is derived from the Growth Inhibition calculation used in the National Cancer Institute's NCI-60 high throughput screen.

Synergy Score Analysis.

Synergy scores were determined using the Chalice Software (Zalicus Inc., Cambridge Mass.). Briefly, to measure combination effects in excess of Loewe additivity, a scalar measure to characterize the strength of synergistic interaction termed the Synergy Score was used. The Synergy Score is calculated as:

Synergy Score=log $f_X$ log $F_Y \Sigma$max(0,$I_{data}$) ($I_{data}$-$I_{Loewe}$)

wherein $I_{data}$ is the observed inhibition at a given combination of drug concentrations.

The calculation for additivity is:

$I_{Loewe}$ that satisfies $(X/X_I)+(Y/Y_I)=1$, where $X_I$ and $Y_I$ are the single agent effective concentrations for the observed combination effect I.

Activity observed in excess of Loewe additivity identifies potential synergistic interaction.

The fractional inhibition for each component agent and combination point in the matrix was calculated relative to the median of all vehicle-treated control wells. The Synergy Score equation integrated the experimentally-observed activity volume at each point in the matrix in excess of a model surface numerically derived from the activity of the component agents using the Loewe model for additivity. Additional terms in the Synergy Score equation (above) were used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels.

Self-Cross-Based Combination Screen Analysis.

Combinations where the synergy score is greater than the mean self-cross plus two standard deviations (2σ's) can be considered candidate synergies at the 95% confidence level.

In order to objectively establish hit criteria for the combination screen analysis, twenty compounds were selected to be self-crossed across the seventeen cell line panel as a means to empirically determine a baseline additive, non-synergistic response. The identity of the twenty self-cross compounds was determined by selecting compounds with a variety of maximum response values and single agent dose response steepness. Those drug combinations which yielded effect levels that statistically superseded those baseline additivity values were considered synergistic.

Compound 2 had varying activity across the seventeen cell line panel. For each cell line, a three-fold, ten-point dose titration was performed in 384-well plate format. For cell lines where the $GI_{50}$ reached inhibition levels of greater than fifty percent, the median $GI_{50}$ was 0.14 μM.

TABLE 6

Synergy scores for treatment of breast cancer cell line panel with Compound 2 and 5-Aza. Synergy scores that exceed the mean self-cross thresholds plus two standard deviations (2σ) are depicted in bold.

| Cell Line | Synergy Score | Mean Self Cross Score + 2σ |
|---|---|---|
| BT-20 | 1.16 | 3.23 |
| BT-474 | 1.35 | 3.37 |
| BT-549 | 2.03 | 3.94 |
| HCC1187 | 4.21 | 4.80 |
| HCC-1428 | 1.56 | 3.22 |
| HCC-1500 | 1.95 | 4.17 |
| HCC1806 | 2.09 | 5.05 |
| HCC1937 | 4.8 | 2.89 |
| HCC70 | 4.61 | 3.45 |
| Hs-578-T | 5.53 | 4.09 |
| MCF7 | 2.75 | 3.07 |
| MDA-MB-157 | 3.98 | 4.68 |

TABLE 6-continued

Synergy scores for treatment of breast cancer cell line panel with Compound 2 and 5-Aza. Synergy scores that exceed the mean self-cross thresholds plus two standard deviations (2σ) are depicted in bold.

| Cell Line | Synergy Score | Mean Self Cross Score + 2σ |
|---|---|---|
| MDA-MB-175-VII | 0.3 | 2.82 |
| MDA-MB-231 | 4.27 | 2.61 |
| MDA-MB-436 | 2.91 | 1.91 |
| MDA-MB-453 | 1.42 | 2.99 |
| MDA-MB-468 | 7.29 | 4.66 |

Conclusion:

As can be seen in Table 6, Compound 2 in combination with 5-Aza showed synergistic effects in multiple breast cancer cell lines, and in particular in basal-like breast cancer cell lines.

Activity of TOR Kinase Inhibitor and Second Active Agents.

Other examples of second active agents that can be tested in the cell viability assays, using for example an ovarian cancer cell line, in combination with a TOR kinase inhibitor are, for example, cytidine analogs.

Other examples of second active agents that can be tested in the cell viability assays, using for example a multiple myeloma cell line, in combination with a TOR kinase inhibitor are, for example, cytidine analogs.

Other examples of second active agents that were tested or can be tested in the cell viability assays, using for example a hepatocellular carcinoma cell line, in combination with a TOR kinase inhibitor are, for example, cytidine analogs.

6.3 In Vivo Assays

DLBCL Xenograft Model.

Human DLBCL (WSU-DLCL2) cancer cell lines are injected into SCID (severe combined immunodeficiency) mice. Cancer cell lines are propagated in culture in vitro. Tumor bearing animals are generated by injecting 1×10$^6$ cells into mice. Following inoculation of animals, the tumors are allowed to grow to a certain size prior to randomization. The mice bearing xenograft tumors ranging between 100 and 400 mm$^3$ are pooled together and randomized into various treatment groups. A TOR kinase inhibitor and a cytidine analog are administered at various dose levels to tumor-bearing mice. Additionally, reference chemotherapeutic agents such as CHOP therapy (combination of cyclophosphamide, doxorubicin, vincristine and prednisone) and negative controls are included in the study. Routes of administration can include subcutaneous (SC), intraperitoneal (IP), intravenous (IV), intramuscular (IM) and oral (PO). Tumor measurements and body weights are taken over the course of the study and morbidity and mortality are recorded. Tumors are measured twice a week using calipers and tumor volumes calculated using the formula of $W^2 \times L/2$.

OCI-Ly10 DLBCL Xenograft Model.

OCI-Ly10 cells are derived from a diffuse-large B-cell lymphoma, a type of non-Hodgkins lymphoma. In brief, female CB.17 SCID mice are inoculated with 5×10$^6$ OCI-Ly10 cells subcutaneously, and tumors are allowed to grow to approximately 50-300 mm$^3$. The mice bearing xenograft with similarly sized tumors are pooled together and randomized into various treatment groups. A typical efficacy study design involves administering one or more compounds at various dose levels and schedules, based on prior single agent studies, to tumor-bearing mice. Tumor volume is measured biweekly for approximately 28 days of treatment using calipers, and tumor volume is calculated using standard methods, for example, using the formula of $W^2 \times L/2$. Tumor volume can optionally be measured further post-treatment. Statistical analysis will be performed using standard statistical methods.

6.4 Compound Formulations

Illustrative formulations of Compound 1 useful in the methods provided herein are set forth in Tables 7-10, below.

TABLE 7

| Ingredients | Amounts mg | % w/w |
|---|---|---|
| Compound 1 | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4.0 |

TABLE 8

| Ingredients | Amounts mg | % w/w |
|---|---|---|
| Compound 1 | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

TABLE 9

| Ingredients | Amounts mg | | | % w/w |
|---|---|---|---|---|
| Compound 1 | 15.0 | 20.0 | 30.0 | 15.38 |
| Lactose monohydrate, NF (Fast Flo 316) | 48.37 | 64.50 | 96.75 | 49.62 |
| Microcrystalline cellulose, NF (Avicel pH 112) | 30.23 | 40.30 | 60.45 | 31.00 |
| Croscarmellose sodium, NF (Ac-Di-Sol) | 2.925 | 3.90 | 5.85 | 3.00 |
| Magnesium Stearate, NF | 0.975 | 1.30 | 1.95 | 1.00 |
| Total | 97.50 | 130.0 | 195.00 | 100 |
| Opadry yellow 03K12429 | 3.9 | | | 4.0 |
| Opadry II Pink 85F94211 | | 5.2 | | 4.0 |
| Opadry Pink 03K140004 | | | 7.8 | 4.0 |

TABLE 10

| Ingredients | Amounts mg | % w/w |
|---|---|---|
| Compound 1 | 45.00 | 15.38 |
| Lactose monohydrate, NF (Fast Flo 316) | 143.955 | 49.22 |
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.70 | 4.0 |

Illustrative formulations of Compound 2 useful in the methods provided herein are set forth in Table 11, below.

TABLE 11

Exemplary Tablet Formulations

| Ingredients | % w/w (mg) Batch # | | | |
|---|---|---|---|---|
| | 1 | 2 | 3 | 4 |
| Compound 2 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

What is claimed is:

1. A method for treating liver cancer or breast cancer, comprising administering an effective amount of a TOR kinase inhibitor in combination with an effective amount of 5 azacytidine to a patient having liver cancer or breast cancer, wherein the TOR kinase inhibitor is 1-ethyl-7-(2-methyl-6-(4H-1,2,4-triazol-3-yl)pyridin-3-yl)-3,4-dihydro-pyrazino[2,3-b]pyrazin-2(1H)-one or 7-(6-(2-hydroxypropan-2-yl)pyridin-3 -yl)-1-(trans-4-methoxycyclohexyl)-3,4-dihydropyrazino[2,3 -b]pyrazin-2(1H)-one or a pharmaceutically acceptable salt, stereoisomer, or tautomer thereof.

2. The method of claim 1, wherein the cancer is a relapsed or refractory cancer.

3. The method of claim 1, wherein the cancer is an advanced cancer.

4. The method of claim 1, wherein the breast cancer is, hormone receptor positive, estrogen receptor positive (ER+, ER+/Her2 or ER+/Her2+), estrogen receptor negative (ER−/Her2+) or triple negative (TN).

5. The method of claim 1, wherein the cancer is a cancer associated with the pathways involving mTOR, PI3K, or Akt kinases and mutants or isoforms thereof.

6. The method of claim 1, wherein the cancer is liver cancer.

7. The method of claim 1, wherein the cancer is breast cancer.

8. The method of claim 1, wherein the TOR kinase inhibitor is 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer, or tautomer thereof.

9. The method of claim 1, wherein the TOR kinase inhibitor is 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer, or tautomer thereof.

\* \* \* \* \*